(12) United States Patent
Fahmy et al.

(10) Patent No.: US 9,737,593 B2
(45) Date of Patent: *Aug. 22, 2017

(54) CARBON NANOTUBE COMPOSITIONS AND METHODS OF USE THEREOF

(71) Applicant: Yale University, New Haven, CT (US)

(72) Inventors: Tarek M. Fahmy, New Haven, CT (US); Lisa D. Pfefferle, Branford, CT (US); Gary L. Haller, Hamden, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/842,782

(22) Filed: Mar. 15, 2013

(65) Prior Publication Data

US 2013/0216581 A1 Aug. 22, 2013

Related U.S. Application Data

(63) Continuation-in-part of application No. 12/933,223, filed as application No. PCT/US2009/037727 on Mar. 19, 2009, now Pat. No. 8,658,178.

(60) Provisional application No. 61/037,798, filed on Mar. 19, 2008.

(51) Int. Cl.
| *A61K 39/385* | (2006.01) |
| *C12N 5/071* | (2010.01) |
| *C12P 21/08* | (2006.01) |
| *C07K 16/00* | (2006.01) |
| *A61K 39/00* | (2006.01) |
| *A61K 39/39* | (2006.01) |
| *A61K 35/17* | (2015.01) |

(52) U.S. Cl.
CPC .............. *A61K 39/00* (2013.01); *A61K 35/17* (2013.01); *A61K 39/0011* (2013.01); *A61K 39/385* (2013.01); *A61K 39/39* (2013.01); *A61K 2039/5158* (2013.01); *A61K 2039/55555* (2013.01); *A61K 2039/6093* (2013.01)

(58) Field of Classification Search
None
See application file for complete search history.

(56) References Cited

U.S. PATENT DOCUMENTS

| 8,629,098 | B2 * | 1/2014 | Fahmy | .................... A61K 39/39 424/489 |
| 2003/0235908 | A1 | 12/2003 | Berenson | |
| 2004/0076681 | A1 | 4/2004 | Dennis | |
| 2004/0202603 | A1 | 10/2004 | Fischer | |
| 2004/0232073 | A1 | 11/2004 | Papadimitrakopoulos | |
| 2005/0147553 | A1 * | 7/2005 | Wong | ..................... B82Y 30/00 423/447.2 |
| 2010/0284965 | A1 * | 11/2010 | Fahmy | ............. A61K 47/48276 424/85.2 |

FOREIGN PATENT DOCUMENTS

WO WO 2009117616 A2 * 9/2009

OTHER PUBLICATIONS

Steenblock et al., 2009, Exp. Opin Biol. Ther. vol. 9: 451-64.*
Erickson, 2009, Biol. Proc. Online. vol. 11:32-51.*
Fadel et al., 2009, Langmuir, vol. 265645-5654.*
Zuany-Amorim et al., 2002, Nat. Rev. vol. 1: 797-807.*
Luthje et al., 2008, Int. Immunol. vol. 20: 949-960.*
Balthasar, et al., "Preparation and characterisation of antibody modified gelatin nanoparticles as drug carrier system for uptake in lymphocytes", Biomaterials, 26(5):2723-32 (2004).
Bianco, et al., "Applications of carbon nanotubes in drug delivery", Curr. Opin, Chem. Biol., 9(6):674-9 (2005).
Bianco, et al., "Biomedical applications of functionalied carbon nanotubes", Chemical Comm., NR 5:571-577 (2005).
Cinke, et al., "Pore structure of raw and puri ed HiPco single-walled carbon nanotubes", Chem. Phys. Lett., 365:69-74 (2002).
Dumortier, at al., "Functionalized carbon nanotubes are non-cytotoxic and preserve the functionality of primary immune cells", Nano Lett., 6:1522-8 (2006).
Fadel, at al., "Enhanced cellular activation with single walled carbon nanotube bundles presenting antibody stimuli", Nano Ltrs, 8(7):2070-76 (2008).
Fahmy Lab,"Enhanced antigen-presentation using carbon nanotube bundles", accessed from Fahmy Lab website, URL:http://www.fahmylab.org/labatory/, accessed Apr. 20, 2011.
Feazell, et al., "Soluble single-walled carbon nanotubes as longboat delivery systems for platinum(IV) anticancer drug design", J. Am. Chem. Soc., 129 (27):8438-9 (2007).vbTab.
Hemraj-Benny, et al., "Effect of ozonolysis on the pore structure, surface chemistry, and bundling of single-walled carbon nanotubes", Jour. Coll. lnterf. Sci., 317(2):375-82 (2008).
Hu, et al., "Nitric Add Purification of Single-Walled Carbon Nanotubes", Jour. Phys. Chem. B, 107:13838-42 (2003).
Jiang, et al., "Protein immobilization on carbon nanotubes via a two-step process of diimide-activated amidation", J. Materials Chemistry,14(6):37-39 (2003).
Kam, et al., "Nanotube molecular transporters: internalization of carbon nanotube-protein conjugates into Mammalian cells", J. Am. Chem. Soc., 126(22):6850-1 (2004).
Karajsnagi, et al., "Structure and function of enzymes adsorbed onto single-walled carbon nanotubes", Langmuir, 20:11594-9 (2004).
Kim, et al., "The ABCs of artificial antigen presentation", Nat. Biotechn., 22:403-10 (2004).

(Continued)

*Primary Examiner* — Amy Juedes
(74) *Attorney, Agent, or Firm* — Pabst Patent Group LLP

(57) ABSTRACT

Carbon nanotube (CNT)-based compositions for activating cellular immune responses are provided. The CNTs function as high surface area scaffolds for the attachment of T cell ligands and/or antigens. The CNT compositions function as artificial antigen-presenting cells (aAPCs) or as modular vaccines. The disclosed CNT aAPCs are efficient at activating T cells and may be used to activate T cells ex vivo or in vivo for adoptive or active immunotherapy.

14 Claims, 16 Drawing Sheets

(56) References Cited

OTHER PUBLICATIONS

Liang, et al., "A Convenient Route to Functionalized Carbon Nanotubes", Nano Lett., 4:1257-60 (2004).
Magrez, et al. "Cellular toxicity of carbon-based nanomaterials", Nano Lett., 6:1121-5 (2006).
Maruyama, et al., "Covalent attachment of protein to the tip of a muitiwallws carbon nanotube without sidewall decoration", J Applied Physics, 102(9):94701. (2007.
Niyogi, et al., "Chemistry of single-walled carbon nanotubes", Acc. Chem. Res., 35(12):1105-13 (2002).
Oelke, et al., "Ex vivo induction and expansion of antigen-specific cytotoxic T cells by HLA-Ig-coated artificial antigen-presenting cells", Nat. Med., 9(5):619-24 (2003).
Ouyang, et al., "Fundamental electronic properties and applications of single-walled walled carbon nanotubes", Acc, of Chem. Res., 35:1018-25 (2002).
Pantarotto, et al., "Synthesis, structural characterization, and immunological properties of carbon nanotubes functionalized with peptides", J. Am. Chem. Soc., 125(20):6160-4 (2003).
Pantarotto, et al., "Translocation of bioactive peptides across cell membranes by carbon nanotubes", Chem. Commun., 1:16-7 (2004).
Park, et al., "Purification strategies and purity visualization techniques for single-walled carbon nanotubes", Journ. Mater. Chem., 16:141-54 (2006).
Porter, et al., "Direct imaging of single-walled carbon nanotubes in cells", Nature, 2:713-7 (2007).
Salvadoe-Morales, et al., "Complement activation and protein adsorption by carbon nanotubes", Molecular Immunology, 43:193-201 (2006).
Shvedova, et al., "Exposure to carbon nanotube material: assessment of nanotube cytotoxicity using human keratinocyte cells", Jour. Tox. Env. Hlth. Pt. A, 66(20):1909-26 (2003).
Sitharaman, et al., "Superparamagnetic gadonanotubes are high-performance MRI contrast agents", Chem. Commun., 31:3915-7 (2005).
Wang and Iqbal, "Vertically oriented single-wall carbon nanotube/ enzyme on silicon as biosensor electrode", Journal of the Minerals, 57:27-29 (2005).
Williams, et al., "Nanotechnology: carbon nanotubes with DNA recognition", Nature, 420(6917):761 (2002).

\* cited by examiner

CARBON NANOTUBE COMPOSITIONS AND METHODS OF USE THEREOF

CROSS REFERENCE TO RELATED APPLICATIONS

This application is a continuation in part of U.S. Ser. No. 12/933,223, which is the National Stage of International Application No. PCT/US09/37727 filed Mar. 19, 2009, which claims priority to and benefit of U.S. Provisional Patent Application No. 61/037,798, filed on Mar. 19, 2008, the contents of which are incorporated by reference in their entirety.

STATEMENT REGARDING FEDERALLY SPONSORED RESEARCH OR DEVELOPMENT

This invention was made with government support awarded by the National Science Foundation under Career Award Number 0747577 to Tarek M. Fahmy. The United States government has certain rights in this invention.

FIELD OF THE INVENTION

The present disclosure generally relates to the field of carbon nanotube compositions and methods for making and using these compositions.

BACKGROUND OF THE INVENTION

T cells are central players in initiating and maintaining immune responses. An important goal of successful immunotherapy is the stimulation of T cell immune responses against targets of interest such as tumors. This can be accomplished in two ways: 1) through immunization with tumor antigens or 2) by isolation of T cells specific to tumor antigens, and expansion of this population outside the body followed by re-transfer into the patient (adoptive transfer immunotherapy).

Preventative vaccines have eliminated smallpox and nearly eliminated polio, two of the worst global infectious diseases. By contrast vaccines for many other infectious diseases, such as malaria and HIV, which involve intracellular pathogens, are poorly developed or simply unavailable. The lack of such vaccines will result in two million unnecessary deaths each year in many parts of the world. Although economic factors play a role, there are a number of significant scientific challenges that have limited the development of vaccines for deadly diseases. First, few if any approaches are available that efficiently prime cell-mediated immunity by direct intracellular delivery of an antigen. Second, 'tunable' adjuvants, that is, adjuvants that can be engineered to optimize the magnitude and direction of an immune response, have not been developed. Third, the general requirement for parenteral (i.e. subcutaneous or intramuscular injection) administration of vaccines, a situation that has made it difficult to deploy vaccines in underdeveloped countries where medical support systems, resources, and even refrigeration are limited. Finally, there is a lack of a general approach to designing oral vaccines targeted to both systemic and mucosal immunity; oral vaccines are significantly less expensive to administer and transport. Thus, there is a critical need for safe and stable vaccine systems that would address these factors.

Some of the most encouraging data regarding immunotherapy come from studies employing adoptive transfer of tumor reactive T cells. Adoptive T cell transfer is an elegant approach to the treatment of infectious and malignant diseases. This therapeutic method involves the ex vivo expansion of T cells, which may be infused into patients to bolster the natural immune response. For example, expanded tumor-specific T cells have been shown to strengthen patient's immune responses to melanoma by infiltrating the tumor site and inducing tumor shrinkage. Researchers have also demonstrated that the adoptive transfer of T cells is a viable therapeutic approach to treating Epstein-Barr virus (EBV) as well as human immunodeficiency virus (HIV)-related infections. Thus, adoptive T cell transfer has potential applications in the treatment of both infectious diseases and cancer.

Despite the successes of these studies, adoptive T cell transfer by clonal expansion is not clinically viable since it does not consistently generate therapeutic numbers of T cells. This shortcoming has prompted the development of an alternative techniques for ex vivo T cell expansion, using artificial antigen presentation to T cells (Prakken, et al., Nat. Med., 6(12):1406-10 (2000); Oelke, et al., Nat. Med., 9(5): 619-24 (2003); Kim, et al., Nat. Biotechn., 22:403-10 (2004)). The development of artificial APCs (aAPCs) is a new effort to generate a reproducible, "off-the shelf" means of stimulating and expanding T cells. Several types of aAPCs have been developed, including nonspecific bead-based systems that are currently used in many research laboratories to sustain the long-term expansion of $CD8^+$ T cells (Oelke, et al., Nat. Med., 9(5):619-24 (2003); Kim, et al., Nat. Biotechn., 22:403-10 (2004)).

Specific expansion of T cells outside the body depends however on efficient methods for displaying protein ligands that stimulate those cells. Ultimately, T cell stimulus intensity depends on the density of bound receptors in the contact area with a surface (Andersen, et al., J. Biol. Chem., 276 (52):49125-32 (2001); Gonzalez, et al., Proc. Natl. Acad. Sci. U.S.A., 102(13):4824-9 (2005)). Regions with a high density of T cell antigen receptors have been termed activated clusters because they are critical for T cell stimulation (Grakoui, et al., Science, 285(5425:221-7 (1999); Monks, et al., Nature, 395(6697):82-6 (1998)). The presence of such high density clusters has also been shown to accelerate T cell activation (Gonzalez, et al., Proc. Natl. Acad. Sci. U.S.A., 102(13):4824-9 (2005)). In the lymph node, the primary site for T cell stimulation, antigen presenting cells are thought to concentrate the presentation of T cell stimuli by trafficking in a dense architectural scaffolding in close proximity to T cells.

It is therefore an object of the invention to provide compositions that provide for high density presentation of ligands to T cell surface receptors.

It is another object of the invention to provide modular vaccine systems which provide for flexible addition of antigens and other elements.

It is another object of the invention to provide methods for activating T cells in vivo and ex vivo using compositions that provide high density ligand presentation.

It is yet another object of the invention to provide methods for activating and expanding T cells in vivo or ex vivo using compositions that provide high density presentation of T cell ligands.

It is still another object of the invention to provide methods for active and adoptive immunotherapy of diseases and disorders using compositions that provide high density presentation of T cell-activating ligands.

SUMMARY OF THE INVENTION

Carbon nanotube (CNT)-based compositions for activating cellular immune responses are provided. The CNTs function as high surface area scaffolds for the attachment of T cell ligands and/or antigens. CNTs may be fabricated using any suitable method. CNTs may be single-walled carbon nanotubes (SWNTs) or multi-walled carbon nanotubes (MWNTs). Proteins may be either covalently or non-covalently attached to the CNTs. The surface area of CNTs may be adjusted by chemical means, such as treatment with acid, prior to attachment of proteins.

CNT compositions that function as artificial antigen-presenting cells (aAPCs) include ligands attached to CNTs that bind to cell surface receptors on T cells, including at least one species of ligand that binds to and activates the T cell receptor. T cell receptor activators may be antigen-specific or polyclonal T cell receptor activators. Suitable antigen-specific T cell receptor activators include antigens bound to MHC/HLA molecules. Exemplary antigens include, but are not limited to, viral antigens, bacterial antigens, parasite antigens, allergens and environmental antigens, tumor antigens or autoantigens. Suitable polyclonal T cell receptor activators include, but are not limited to, antibodies that crosslink the T cell receptor. CNT aAPCs may also include one or more costimulatory or T cell adhesion molecules to facilitate T cell attachment to the aAPCs and T cell activation.

CNT compositions that function as modular vaccines do not directly activate T cells by binding to T cell surface receptors, but rather, facilitate the delivery of antigens to natural APCs in vivo. The modular CNT vaccine compositions include antigens and may further include elements that facilitate antigen uptake by APCs, or APC activation. Suitable additional elements include adjuvants, dendritic cell recognition elements, epithelial cell recognition elements, or molecules which protect the vaccine compositions from degradation in low-pH environments.

Methods of using the disclosed CNT aAPCs and CNT vaccine compositions to activate T cells are provided. The CNT aAPC compositions are extremely efficient activators of T cells. The examples demonstrate that anti-CD3 antibodies adsorbed onto SWNT bundles stimulate cells more efficiently than equivalent concentrations of soluble anti-CD3 antibodies. Furthermore, SWNT bundles bound to anti-CD3 antibodies are more efficient at activating T cells than other high surface area compositions, such as activated carbon and polystyrene and C60 nanoparticles, even when normalized by surface area. This indicates that SWNTs possess unique properties in addition to their high surface area that make them ideally suited to function as scaffolds for aAPCs and make them superior to existing aAPC scaffolds.

Methods for using the CNT aAPCs for ex vivo activation of T cells for adoptive immunotherapy are provided. The methods include isolating a population of T cells from a subject to be treated, activating the T cells with the CNT aAPCs, expanding the T cells, and administering the T cells to the subject to be treated in an amount effective to induce an immune response. Methods for adoptive immunotherapy of conditions associated with overactivation of the immune system by ex vivo activation of regulatory T cells are also provided.

Methods for active immunotherapy using the disclosed CNT aAPCs or CNT vaccine compositions are also provided.

DETAILED DESCRIPTION OF THE INVENTION

I. Definitions

Figure 1:
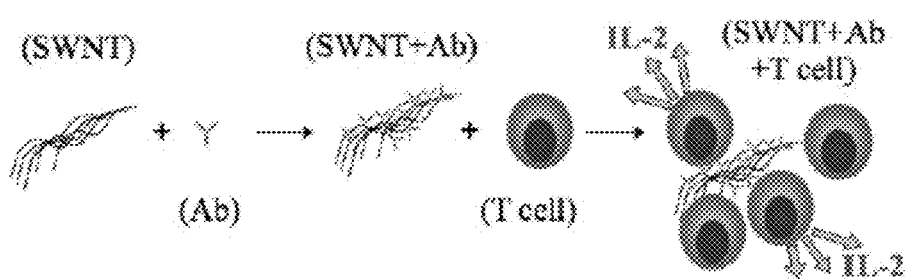
FIG. 1 is a schematic showing activation of T cells using single-walled nanotube (SWNT) scaffolds with adsorbed anti-CD3 antibodies (Ab). The first step is adsorption of anti-CD3 antibodies onto the SWNT scaffold. Following washing, the anti-CD3-adsorbed SWNTs (SWNT+Ab) are incubated with T cells and the amount of T cell activation can be measured by determining the amount of cytokines, such as Il-2, released by the T cells.

An "antigen" is defined herein as a molecule which contains one or more epitopes that will stimulate a host's immune system to make a cellular antigen-specific immune response, and/or a humoral antibody response. Antigens can be peptides, proteins, polysaccharides, saccharides, lipids, nucleic acids, and combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components. An antigen may be an oligonucleotide or polynucleotide which expresses an antigen. Antigens can be natural or synthetic antigens, for example, haptens, polyepitopes, flanking epitopes, and other recombinant or synthetically derived antigens (Bergmann, et al., *Eur. J. Immunol.*, 23:2777-2781 (1993); Bergmann, et al., *J. Immunol.*, 157:3242-3249 (1996); Suhrbier, *Immunol. and Cell Biol.*, 75:402-408 (1997).

A "tumor-specific antigen" is defined herein as an antigen that is unique to tumor cells and does not occur in or on other cells in the body.

A "tumor-associated antigen" is defined herein as an antigen that is not unique to a tumor cell and is also expressed in or on a normal cell under conditions that fail to induce an immune response to the antigen.

As used herein, the term "isolated" describes a compound of interest (e.g., either a polynucleotide or a polypeptide) that is in an environment different from that in which the compound naturally occurs, e.g., separated from its natural milieu such as by concentrating a peptide to a concentration at which it is not found in nature. "Isolated" includes compounds that are within samples that are substantially enriched for the compound of interest and/or in which the compound of interest is partially or substantially purified.

As used herein, the term "polypeptide" refers to a chain of amino acids of any length, regardless of modification (e.g., phosphorylation or glycosylation).

As used herein, a "variant" polypeptide contains at least one amino acid sequence alteration (addition, deletion, substitution, preferably conservative i.e., not substantially changing the function except in magnitude) as compared to the amino acid sequence of the corresponding wild-type polypeptide.

As used herein, an "amino acid sequence alteration" can be, for example, a substitution, a deletion, or an insertion of one or more amino acids.

As used herein, a "fragment" of a polypeptide refers to any subset of the polypeptide that is a shorter polypeptide of the full length protein. Generally, fragments will be five or more amino acids in length.

As used herein, "conservative" amino acid substitutions are substitutions wherein the substituted amino acid has similar structural or chemical properties.

As used herein, "non-conservative" amino acid substitutions are those in which the charge, hydrophobicity, or bulk of the substituted amino acid is significantly altered.

As used herein, "isolated nucleic acid" refers to a nucleic acid that is separated from other nucleic acid molecules that are present in a mammalian genome, including nucleic acids that normally flank one or both sides of the nucleic acid in a mammalian genome. As used herein with respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "host cell" refers to prokaryotic and eukaryotic cells into which a recombinant expression vector can be introduced.

As used herein, "transformed" and "transfected" encompass the introduction of a nucleic acid (e.g. a vector) into a cell by a number of techniques known in the art.

As used herein, the phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$, or $10^{10}$ $M^{-1}$. Affinities greater than $10^8$ $M^{-1}$ are preferred.

As used herein, the terms "antibody" or "immunoglobulin" include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.*, 79:315-321 (1990); Kostelny et al., *J. Immunol.*, 148, 1547-1553 (1992).

As used herein, the terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids, in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke, et al., *J. Inf. Dis.*, 170:1110-19 (1994)), by antigen-dependent killing (cytotoxic T lymphocyte assay, Tigges, et al., *J. Immunol.*, 156:3901-3910) or by cytokine secretion.

As used herein, the terms "immunologic", "immunological" or "immune" response is the development of a humoral (antibody mediated) and/or a cellular (mediated by antigen-specific T cells or their secretion products) response directed against an antigen. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, a "costimulatory polypeptide" or a "costimulatory molecule" is a polypeptide that, upon interaction with a cell-surface molecule on T cells, enhances T cell responses, enhances proliferation of T cells, enhances production and/or secretion of cytokines by T cells, stimulates differentiation and effector functions of T cells or promotes survival of T cells relative to T cells not contacted with a costimulatory peptide.

II. Carbon Nanotube Compositions

Compositions based on carbon nanotubes (CNTs) for activating cellular immune responses are disclosed. In one embodiment, the CNT compositions contain ligands for T cell surface receptors and function as artificial antigen-presenting cell (aAPCs) to directly activate T cells either in vivo or ex vivo. In another embodiment, the CNT compositions contain antigens and are used as modular vaccine systems to deliver the antigen to professional APCs to activate T cells in vivo.

A. Carbon Nanotubes

The compositions include carbon nanotubes (CNTs) as high surface area scaffolds for the attachment or ligands and/or antigens. A carbon nanotube is a crystalline carbon with a structure in which a thin layer of graphite crystal is rolled-up into the shape of a cylinder. CNTs are formed of carbons atoms in the form of a graphene structure, which is a flat or curved layer formed by arranging six-membered rings of carbon atoms in a honeycomb. A carbon nanotube is a cylindrical structure in which such a layer is rolled-up in one direction. In general, those with a diameter of several nanometers to several ten of nanometers and a length of several ten times to not less than several thousand times longer than its diameter are called "carbon nanotubes".

CNTs that form the scaffold may be either single-walled CNTs (SWNTs) or multi-walled CNTs (MWNTs). In a preferred embodiment, the compositions contain SWNTs. SWNTs are formed by a single graphene layer rolled-up in the shape of a cylinder. MWNTs are formed by two or more graphene layers rolled-up in the shape of a cylinder. Single-walled carbon nanotubes may assume three types of shapes, termed "armchair", "zigzag", and "chiral", depending on how the six-membered rings are arranged.

SWNTs have applications ranging from electronics (Ouyang, et al., *Acc. of Chem. Res.*, 35:1018-25 (2002)), drug delivery (Feazell, et al., *J. Am. Chem. Soc.*, 129(27):8438-9 (2007); Kam, et al., *J. Am. Chem. Soc.*, 126(22):6850-1 (2004)), imaging (Sitharaman, et al., *Chem. Commun.*, (31): 3915-7 (2005)) and biosensing (Wang and Iqbal, *Journal of the Minerals*, 57:27-29 (2005)).

1. Methods for Making CNTs

CNTs may be fabricated using any suitable method. CNTs are normally produced by various methods, such as arc-discharge methods, laser evaporation methods, thermal chemical vapor deposition (CVD) methods, and flowing vapor deposition methods. The arc-discharge method is a method of growing CNTs by means of arc discharge using carbon electrodes. The arc-discharge method is capable of producing an enormous amount of CNTs. The laser evaporation method typically forms CNTs by evaporating part of a graphite electrode by means of a laser. The thermal CVD method grows carbon nanotubes at a high temperature by thermally decomposing hydrocarbon, which is a carbon source, on a substrate with a metal catalyst thereon. The flowing vapor deposition method generates carbon nanotubes by making an organic transition metal compound and a hydrocarbon compound, which is a carbon source, both flowing with a carrier gas, react with each other at a high temperature.

2. Methods for Attaching Proteins to CNTs

The CNT compositions contain attached proteins. Proteins may be attached to CNTs covalently through reaction with the functionalized CNT surface or non-covalently by non-specific adsorption (Kam, et al., *J. Am. Chem. Soc.*, 126(22):6850-1 (2004); Karajanagi, et al., *Langmuir*, 20:11594-9 (2004)).

CNTs have a high capacity for protein adsorption due to their high surface area. The surface area of CNTs available for protein adsorption may also be adjusted by altering the surface chemistry of the CNT. In this way, accessible surfaces that are a priori not available for protein adsorption may be made accessible through chemical treatment. In one embodiment, CNTs are subjected to treatment with acid prior to protein adsorption. Recent studies have demonstrated that acid treatment of SWNTs induces defects on the surface of the nanotubes (Hu, et al., *Jour. Phys. Chem. B*, 107:13838-42 (2003)), as well as promote de-bundling (Liang, et al., *Nano Lett.*, 4:1257-60 (2004)), which can be correlated with an increase in surface area (Hemraj-Benny, et al., *Jour. Coll. Interf Sci.*, 317(2):375-82 (2008)). In one embodiment, CNTs are treated with nitric acid prior to protein adsorption, which introduces carboxylic acid groups at the open ends leading to sites of defects and hence increasing the capacity for protein adsorption (Hu, et al., *Jour. Phys. Chem. B*, 107:13838-42 (2003)). In one embodiment, the CNTs are reduced following acid treatment. For example, following nitric acid treatment, CNTs may be treated with lithium borohydride to preferentially reduce the oxygenated groups created by the acid treatment, favoring the dispersion of the CNTs in solution (U.S. Published Application No. 2004/0232073) and further increasing the surface area available for protein adsorption. The examples below demonstrate that treatment of CNTs with 3M HNO$_3$ significantly increases surface area of SWNTs, which is further increased by subsequent treatment with LiBH$_4$.

In addition to non-specific adsorption, proteins can also be attached to CNTs through covalent interactions through various functional groups. Functionality refers to conjugation of a molecule to the surface of the CNT via a functional chemical group (carboxylic acids, aldehydes, amines, sulfhydryls and hydroxyls) present on the CNT and present on the molecule to be attached. Biochemical functionalization of CNTs using various proteins for potential applications in biological systems are described by Kam, et al., *J. Am. Chem. Soc.*, 126(22):6850-1 (2004); Bianco, et al., *Curr. Opin. Chem. Biol.*, 9(6):674-9 (2005); Pantarotto, et al., *J. Am. Chem. Soc.*, 125(20):6160-4 (2003); Williams, et al., *Nature*, 420(6917):761 (2002); Pamtarotto, et al., *Chem. Commun.*, 1:16-7 (2004).

B. CNT-Based Artificial Antigen Presenting Cells (aAPCs)

In one embodiment, the CNT compositions function as aAPCs. In this embodiment, proteins that are covalently or non-covalently attached to CNTs are T cell ligands that bind to cell surface molecules on T cells. Typically, the ligands are polypeptides. Suitable T cell ligands include, but are not limited to, antigen-specific and polyclonal T cell receptor ligands, co-stimulatory molecules, and T cell targeting and adhesion molecules. CNT aAPCs may be associated with a single species of functional T cell ligand or may be associated with any combination of disclosed T cell ligands in any ratio.

Suitable T cell ligands may contain the entire protein that binds to the desired cell surface receptor, or may contain only a portion of the ligand. For example, it may be desirable to remove a portion of the ligand that has an undesirable biological activity, or it may be desirable to remove a portion of the ligand to enable attachment of the CNT. The only requirement when a portion of a ligand is present is that the portion of the ligand substantially retains the ligand's receptor binding activity. The terms "portion" and "fragment" are used herein interchangeably.

Suitable T cell ligands include variant ligands. As used herein, a "variant" polypeptide contains at least one amino acid sequence alteration as compared to the amino acid sequence of the corresponding wild-type polypeptide. An amino acid sequence alteration can be, for example, a substitution, a deletion, or an insertion of one or more amino acids.

A variant polypeptide can have any combination of amino acid substitutions, deletions or insertions. In one embodiment, variant polypeptides have an integer number of amino acid alterations such that their amino acid sequence shares at least 60, 70, 80, 85, 90, 95, 97, 98, 99, 99.5 or 100% identity with an amino acid sequence of a corresponding wild type amino acid sequence. In a preferred embodiment, variant polypeptides have an amino acid sequence sharing at least 60, 70, 80, 85, 90, 95, 97, 98, 99, 99.5 or 100% identity with the amino acid sequence of a corresponding wild type polypeptide.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch (*J. Mol. Biol.*, 48:443-453 (1970)); 2) BLOSUM62 comparison matrix from Hentikoff and Hentikoff (*Proc. Natl. Acad. Sci. U.S.A.*, 89:10915-10919 (1992)) 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)*100. For this calculation, alignment length includes internal gaps but does not include terminal gaps.

Amino acid substitutions in variant polypeptides may be "conservative" or "non-conservative". As used herein, "conservative" amino acid substitutions are substitutions wherein the substituted amino acid has similar structural or chemical properties, and "non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain.

Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glu, Gln); polar, positively charged residues (His, Arg, Lys); large aliphatic, nonpolar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Variant polypeptides may be modified by chemical moieties that may be present in polypeptides in a normal cellular environment, for example, phosphorylation, methylation, amidation, sulfation, acylation, glycosylation, sumoylation and ubiquitylation. Variant polypeptides may also be modified with a label capable of providing a detectable signal, either directly or indirectly, including, but not limited to, radioisotopes and fluorescent compounds.

Variant polypeptides may also be modified by chemical moieties that are not normally added to polypeptides in a cellular environment. Such modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues can be converted to asparaginyl and glutaminyl residues by reaction with ammonia. Polypeptides may also include one or more D-amino acids that are substituted for one or more L-amino acids.

Polypeptides to be attached to CNTs may also be coupled to other polypeptides to form fusion proteins. Exemplary polypeptides have a first fusion partner including all or a part of a T cell ligand fused (i) directly to a second polypeptide or, (ii) optionally, fused to a linker peptide sequence that is fused to the second polypeptide.

1. T Cell Receptor Activators
  a. Antigen-Specific T Cell Activators

Antigen molecules are recognized by the immune system after internal processing by natural APCs (Lanzavecchia, *Curr. Opin. Immunol.*, 8:348-54 (1996)). In order to present an antigen, the antigen is broken down into small peptidic fragments by enzymes contained in vesicles in the cytoplasm of the APCs. The enzymes are part of a complex of proteolytic enzymes called a proteosome. Most cells have several different types of proteosomes with differing combinations of specificities, which they use to recycle their intracellular proteins. The peptides produced by the proteosomes are generated in the cytosol and transported into the Golgi, where they are linked to cellular major histocompatibility complex (MHC) molecules. These are referred to as human leukocyte antigens, or "HLAs", in human. MHC and HLA are used interchangeably herein unless specified otherwise.

i. HLA and MHC Molecules

In one embodiment, the CNT aAPCs described herein contain antigen-presenting molecules having determinants which match that of a selected subject or which match any known antigen-presenting molecule determinants. The antigen-presenting molecules may be MHC/HLA class I or class II molecules.

There are two types of HLA molecules used for antigen presentation, class I and class II molecules. HLA class I molecules are expressed on the surface of all cells and HLA class II are expressed on the surface of a specialized class of cells called professional APCs. HLA class II molecules bind primarily to peptides derived from proteins made outside of an APC, but can present self (endogenous) antigens. In contrast, HLA class I molecules bind to peptides derived from proteins made inside a cell, including proteins expressed by an infectious agent (e.g., such as a virus) in the cell and by a tumor cell. When the HLA class I proteins reach the surface of the cell these molecules will thus display any one of many peptides derived from the cytosolic proteins of that cell, along with normal "self" peptides being synthesized by the cell. Peptides presented in this way are recognized by T-cell receptors which engage T-lymphocytes in an immune response against the antigens to induce antigen-specific cellular immunity.

Class I transplantation antigens of the major histocompatibility complex (MHC) or HLA are cell surface glycoproteins which present antigens to cytotoxic T-cells. They are heterodimeric and composed of a polymorphic, MHC-encoded, approximately 45 kD heavy chain, which is non-covalently associated with an approximately 12 kD β-2 microglobulin (β-2 m) light chain.

The extracellular portion of the MHC Class I heavy chain is divided into three domains, α-1, α-2, and α-3, each approximately 90 amino acids long and encoded on separate exons. The α-3 domain and β-2 m are relatively conserved and show amino-acid sequence homology to immunoglobulin constant domains. The polymorphic α-1 and α-2 domains show no significant sequence homology to immunoglobulin constant or variable region, but do have weak sequence homology to each other. The membrane-distal polymorphic α-1 (approximately 90 amino acids) and α-2 (approximately 92 amino acids) domains each include four anti-parallel, β-pleated sheets bordered by one α-helical regions, (the first from the α-1 and the second from the α-2 domain). The α-2 domain is attached to the less-polymorphic, membrane-proximal α-3 (approximately 92 amino acids) domain which is followed by a conserved transmembrane (25 amino acids) and an intra-cytoplasmic (approximately 30 amino acids) segment. The rat, mouse, and human Class I MHC molecules are believed to have similar structural characteristics based upon known nucleotide sequences of the various MHC Class I molecules.

The classical class I gene family includes the highly polymorphic human class I molecules HLA-A, -B, and -C, and murine class I (i.e., H-2) molecules D, K, and L. A series of structural relatives (non-classical class I molecules) has been found in humans (e.g., HLA-E, -F, -G, -H, -I, and -J; and CD1) and mice (Q, T, M, and CD1) (Shawar, et al., *Annu. Rev. Immunol.*, 12:839-880 (1994)). These molecules have the typical structure of an antigen-presenting molecule, where a polymorphic heavy chain is noncovalently associated with the conserved β2-M subunit.

In the case of human class I determinants, the determinant can be a polypeptide encoded by any of the known HLA genetic loci, as well as polypeptides encoded by genetic loci not yet discovered so long as these can present antigen to a T cell in a manner effective to activate the T cell receptor. Examples of known HLA class I genetic loci include for HLA-A: A1, A2, A3, A11, A23, A24, A25, A26, A28, A29, A30, A31, A32 and Aw33; for HLA-B: B7, B13, B18, B27, B35, B37, B38, B39, Bw31, Bw42, B44, B45, B49, Bw50, B51, Bw52, Bw53, Bw54, Bw55, Bw57, Bw58, Bw60, Bw61, Bw62, Bw63, Bw64 and Bw65; for HLA-C: Cw1$^b$, Cw2, Cw3, Cw4, Cw5, Cw6, Cw7 and Cw8.

The amino acid sequences of mammalian MHC class II alpha and beta chain proteins, as well as nucleic acids encoding these proteins, are also well known in the art and available from numerous sources including GenBank. Exemplary sequences are provided in Auffray, et al., *Nature*, 308(5957):327-333 (1984) (human HLA DQa); Larhammar, et al., *Proc. Natl. Acad. Sci. U.S.A.*, 80(23):7313-7317 (1983) (human LILA DQβ); Das, et al., *Proc. Natl. Acad. Sci. U.S.A.*, 80 (12): 3543-3547 (1983) (human HLA DRα); Tonnelle, et al., *EMBO J.*, 4(11):2839-2847 (1985) (human HLA DRβ); Lawrence, et al., *Nucleic Acids Res.*, 13(20): 7515-7528 (1985) (human HLA DPα); and Kelly and Trowsdale, *Nucl. Acids Res.*, 13(5):1607-1621 (1985) (human HLA DPβ).

The MHC class I or class II polypeptide selected for use with the CNT aAPCs is typically encoded by genetic loci present in the subject to be treated.

ii. Antigens

MHC/HLA class I or class II molecules are used to present antigens to T cells to activate and expand T cells specific to the antigen. Antigens can be peptides, polypeptides, proteins, polysaccharides, saccharides, lipids, nucleic acids, or combinations thereof. Because CTL epitopes usually comprise 8-10 amino acid long (Townsend, et al., *Annu. Rev. Immunol.*, 7:601-624 (1989); Monaco, *Cell*, 54:777-785 (1992); Yewdell, et al., *Adv. in Immunol.*, 52:1-123 (1992)), in one embodiment, antigens are short polypeptides. Antigenic polypeptides may be about 5 to 40 amino acids, preferably 6 to 25 amino acids, more preferably 8 to 10 amino acids, in length. Examples of antigens presented in various immune responses are described in more detail below and are generally known in the art (Engelhard, *Curr. Opin. Immun.*, 6:13-23 (1994)).

Suitable antigens are known in the art and are available from commercial government and scientific sources. Criteria for identifying and selecting effective antigenic peptides (e.g., minimal peptide sequences capable of eliciting an immune response) can be found in the art. For example, Apostolopoulos, et al. (*Curr. Opin. Mol. Ther.*, 2:29-36 (2000)), discusses the strategy for identifying minimal antigenic peptide sequences based on an understanding of the three-dimensional structure of an antigen-presenting molecule and its interaction with both an antigenic peptide and T-cell receptor. Shastri, (*Curr. Opin. Immunol.*, 8:271-7 (1996)), disclose how to distinguish rare peptides that serve to activate T cells from the thousands peptides normally bound to MHC molecules.

The antigen can be derived from any source including, but not limited to, a virus, bacterium, parasite, plant, protozoan, fungus, tissue or transformed cell such as a cancer or leukemic cell. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic polypeptide. The DNA may be in the form of vector DNA such as plasmid DNA.

Antigens may be provided as single antigens or may be provided in combination. Antigens may also be provided as complex mixtures of polypeptides or nucleic acids.

Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia*.

Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.e. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale,* and *Sorghum*, the orders of Asterales and Urticales including i.a. herbs of the genera *Ambrosia, Artemisia,* and *Parietaria*. Other allergen antigens that may be used include allergens from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenocepphalides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

Tumor Antigens

The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

Self Antigens or Autoantigens

The antigen may also be a self-antigen or an autoantigen. Antigens may be antigens of any autoimmune or inflammatory disease or disorder including, but not limited to, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia greata, allergic responses due to arthropod bite reactions, Crohn's disease, ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

Preferred autoantigens include, but are not limited to, at least a portion of a thyroid-stimulating hormone receptor, pancreatic P cell antigens, epidermal cadherin, acetyl choline receptor, platelet antigens, nucleic acids, nucleic acid protein complexes, myelin protein, thyroid antigens, joint antigens, antigens of the nervous system, salivary gland proteins, skin antigens, kidney antigens, heart antigens, lung antigens, eye antigens, erythrocyte antigens, liver antigens and stomach antigens.

Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor.

Examples of antigens involved in graft rejection include antigenic components of the graft to be transplanted into the graft recipient such as heart, lung, liver, pancreas, kidney, and neural graft components.

b. Polyclonal T Cell Activators

In another embodiment, the CNT aAPCs contain polyclonal T cell receptor activators that activate T cells in the absence of specific antigens. Suitable polyclonal T cell activators include the mitogenic lectins concanavalin-A (ConA), phytohemagglutinin (PHA) and pokeweed mitogen (PWM).

Other suitable polyclonal T cell activators include antibodies that crosslink the T cell receptor/CD3 complex. Exemplary antibodies that crosslink the T cell receptor include the HIT3a, UCHT1 and OKT3 monoclonal antibodies.

2. Costimulatory and T Cell Adhesion Molecules

In addition to ligation of the T cell receptor, activation and proliferation of lymphocytes are regulated by both positive and negative signals from costimulatory molecules. The most extensively characterized T cell costimulatory pathway is B7-CD28, in which B7-1 (CD80) and B7-2 (CD86) each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow, et al., *Annu. Rev. Immunol.*, 14:233-258 (1996); Chambers and Allison, *Curr. Opin. Immunol.*, 9:396-404 (1997); and Rathmell and Thompson, *Annu. Rev. Immunol.*, 17:781-828 (1999)).

The CNT aAPCs described herein may contain one or more species of co-stimulatory molecule. Exemplary co-stimulatory molecules, also referred to as "co-stimulators", include, but are not limited to, CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. Other exemplary co-stimulatory molecules that can be used include antibodies that specifically bind with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83. Other suitable costimulatory molecules include, but are not limited to, costimulatory variants and fragments of the natural ligands described above.

Adhesion molecules may be included for the purpose of enhancing the binding association between the CNT aAPCs and T cells. Suitable adhesion molecules include, but are not limited to, LFA-1, CD49d/29(VLA-4), CD11a/18, CD54 (ICAM-1), and CD106(VCAM) and antibodies to their ligands. Other suitable adhesion molecules include antibodies to selectins L, E, and P.

C. Composite Nanotube Particulate Compositions

In one embodiment, CNT compositions that function as aAPCs are composite carbon nanotube-polymer nanoparticle (CNP) compositions. In this embodiment, proteins that are covalently or non-covalently attached to CNTs are T cell ligands that bind to cell surface molecules on T cells. In some embodiments, any of the CNT aAPCs described above can be used in a CNP composition. The CNP compositions have bound to or present on the CNT surface one or more polymer nanoparticles. The nanoparticles are typically composed of a biodegradable and biocompatible polymer matrix. Immunostimulatory agents are present on, incorporated within, or associated covalently or non-covalently with the polymer matrix. The examples presented below demonstrate that CNP compositions enhanced T cell stimulation to a level comparable to clinically relevant standards using a thousand-fold less soluble IL-2. CNP-expanded T cells show enhanced effector function and significantly delay tumor growth. These results demonstrate the potential of CNP compositions for T cell immunotherapy, especially for adoptive immunotherapies.

In preferred embodiments the CNP compositions containing a T cell ligand and a nanoparticle contain one or more magnetic particles. The magnetic particles will in some cases be present on or encapsulated within the nanoparticle. In some embodiments the magnetic particles will be a second nanoparticle that is bound to or present on the CNT surface, or will be present on or encapsulated within a second nanoparticle that is bound to or present on the CNT surface. The examples presented below demonstrate that CNPs containing magnetic particles exhibited room temperature superparamagnetic properties. Room temperature magnetism allowed for magnetic separation of activated T cells after CNP enrichment.

1. Antigens

The disclosed CNPs may contain any suitable antigen or combination of antigens. Exemplary antigens are discussed above with respect to CNT aAPC compositions.

2. Polymer Nanoparticles

The CNP compositions have bound to or present on the CNT surface one or more polymer nanoparticles. In some embodiments, a therapeutic, diagnostic, and/or prophylactic agent is covalently associated with a polymeric matrix. An immunostimulatory agent can in associated with the polymeric matrix or encapsulated within the polymeric matrix. Association can be covalent or non-covalent. In some embodiments, covalent association is mediated by a linker (e.g., an aliphatic or heteroaliphatic linker). In some embodiments, a therapeutic, diagnostic, and/or prophylactic agent is non-covalently associated with a polymeric matrix. In some embodiments, a therapeutic, diagnostic, and/or prophylactic agent is associated with the surface of, encapsulated within, surrounded by, and/or dispersed throughout a polymeric matrix.

A wide variety of polymers and methods for forming particles therefrom are known in the art of drug delivery. In some embodiments, the matrix of a particle comprises one or more polymers. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers are organic polymers.

Examples of polymers include polyalkylenes (e.g., polyethylenes), polycarbonates (e.g., poly(1,3-dioxan-2one)), polyanhydrides (e.g., poly(sebacic anhydride)), polyhydroxyacids (e.g., poly(.beta.-hydroxyalkanoate)), polyfumarates, polycaprolactones, polyamides (e.g., polycaprolactam), polyacetals, polyethers, polyesters (e.g., polylactide, polyglycolide), poly(orthoesters), polyvinyl alcohols, polyurethanes, polyphosphazenes, polyacrylates, polymethacrylates, polycyanoacrylates, polyureas, polystyrenes, polyamines, poly(arylates), polycarbonates, poly(propylene fumarates), polyhydroxyalkanoates, polyketals, polyesteramides, poly(dioxanones), polyhydroxybutyrates, polyhydroxyvalyrates, polyorthocarbonates, poly(vinyl pyrrolidone), polyalkylene oxalates, polyalkylene succinates, poly(malic acid), poly(methyl vinyl ether), and poly(maleic anhydride). In some embodiments, polymers include polymers which have been approved for use in humans by the United States Food and Drug Administration (U.S.F.D.A.) under 21 C.F.R. .sctn.177.2600, including but not limited to polyesters (e.g., polylactic acid, polyglycolic acid, poly (lactic-co-glycolic acid)), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group).

In some embodiments, polymers may be modified with one or more moieties and/or functional groups. Any moiety or functional group can be used. In some embodiments, polymers may be modified with polyethylene glycol (PEG), with a carbohydrate, and/or with acyclic polyacetals derived from polysaccharides (Papisov, 2001, ACS Symposium Series, 786:301). In some embodiments, polymers may be modified with PEG.

In some embodiments, polymers may be modified with a lipid or fatty acid group, properties of which are described in further detail below. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; lactide-PEG copolymers (e.g., PLA-PEG copolymers); glycolide-PEG copolymers (e.g., PGA-PEG copolymers); copolymers of lactide and glycolide (e.g., PLGA); copolymers of lactide, glycolide, and PEG (e.g., PLGA-PEG copolymers); and derivatives thereof In some embodiments, polyesters include, for example, polyanhydrides, poly(ortho ester), poly(ortho ester)-PEG copolymers, poly(caprolactone), poly(caprolactone)-PEG copolymers, polylysine, polylysine-PEG copolymers, poly(ethylene imine), poly (ethylene imine)-PEG copolymers, poly(L-lactide-co-L-lysine), poly(serine ester), poly(4-hydroxy-L-proline ester), poly[.alpha.-(4-aminobutyl)-L-glycolic acid], and derivatives thereof.

In certain embodiments, a polymer may be PLA. In certain embodiments, a polymer may be PGA. In certain embodiments, a polymer may be PLGA. In certain embodiments, a polymer may be PEG. In certain embodiments, a polymer may be PEG-PLA. In certain embodiments, a polymer may be PEG-PGA. In certain embodiments, a polymer may be PEG-PLGA. In certain embodiments, a polymer may be a PEG-PLA/PLA blend. In certain embodiments, a polymer may be a PEG-PGA/PGA blend. In certain embodiments, a polymer may be a PEG-PLGA/PEG-PLGA blend. In certain embodiments, a polymer may be a PEG-PLA/PGA blend. In certain embodiments, a polymer may be PEG-PLA/PLGA blend. In certain embodiments, a polymer may be a PEG-PGA/PLA blend. In certain embodiments, a polymer may be a PEG-PLGA/PLA blend. In certain embodiments, a polymer may be a PEG-PLGA/PGA blend. In certain embodiments, a polymer may be a PEG-PGA/PLGA blend. In certain embodiments, any of the foregoing may comprise a modified PEG (e.g. methoxy(polyethylene glycol)). For example, a polymer may be methoxy(polyethylene glycol)-PLA. In some embodiments, a polymer may comprise any combination or blend of the foregoing.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used is characterized by a lactic acid:glycolic acid ratio of approximately 85:15, approximately 75:25, approximately 60:40, approximately 65:35, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633). Poly(4-hydroxy-L-proline ester) was recently demonstrated to condense plasmid DNA through electrostatic interactions, and to mediate gene transfer (Putnam et al., 1999, Macromolecules, 32:3658; and Lim et al., 1999, J. Am. Chem. Soc., 121:5633). These new polymers are less toxic than poly(lysine) and PEI, and they degrade into non-toxic metabolites.

In some embodiments, polymers can be anionic polymers. In some embodiments, anionic polymers comprise carboxyl, sulfate, or groups. To give but a few examples, anionic polymers include, but are not limited to, dextran sulfate, heparan sulfate, alginic acid, polyvinylcarboxylic acid, and arabic acid carboxymethylcellulose. In some embodiments, anionic polymers are provided as a salt (e.g., sodium salt).

In some embodiments, a polymer may be a carbohydrate, properties of which are described in further detail below. In some embodiments, a carbohydrate may be a polysaccharide comprising simple sugars (or their derivatives) connected by glycosidic bonds, as known in the art. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

In some embodiments, a polymer may be a protein or peptide, properties of which are described in further detail below. Exemplary proteins include, but are not limited to, albumin, collagen, gelatin, poly(amino acid) (e.g., polylysine), and antibodies.

In some embodiments, a polymer may be a polynucleotide. Exemplary polynucleotides include, but are not limited to, DNA, RNA, etc.

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used without undergoing a cross-linking step.

It is further to be understood that controlled release polymer systems may be a homopolymer, block copolymer, diblock triblock, multiblock copolymer, linear polymer, dendritic polymer, branched polymer, graft copolymer, blend, mixture, and/or adduct of any of the foregoing and other polymers.

3. Immunostimulatory Agents

Either specific and non-specific immunostimulants can be bound to, or encapsuled within, the formulations. Suitable immunostimulants are known and available. Suitable adjuvants are discussed below.

4. Magnetic Particles

"Magnetic material" as used herein refers to any material that induces a force or movement when introduced into a magnetic field. Suitable magnetic materials include, but are not limited to, ferromagnetica and superparamagnetic materials, such as iron containing compounds, martensitic stainless steels (e.g. 400 series), iron oxides($Fe_2O_3$, $Fe_3O_4$), neodymium iron boron, alnico (AlNiCo), and samarium cobalt ($SmCo_5$).

D. CNT-Based Modular Vaccine Compositions

In another embodiment, the CNT compositions are modular vaccine compositions that function to deliver antigens to antigen-presenting cells in vivo. In this embodiment, the CNT compositions do not directly activate T cells by binding to T cell surface receptors, but rather facilitate the delivery of large amounts of antigen to natural APCs, which, in turn, activate T cells and other immune cells. The examples below demonstrate that immunization of mice with a model antigen (ovalbumin) adsorbed onto SWNTs causes priming of T cell activation to a greater extent than immunization with ovalbumin adsorbed onto alum, which is widely used as an adjuvant. Therefore, CNTs function in this embodiment both as a carrier for antigens and also as immune adjuvants.

The CNT vaccine compositions may include elements that facilitate antigen uptake by APCs and APC activation, including, but not limited to, additional adjuvants, dendritic cell recognition elements, epithelial cell recognition elements, or molecules which protect the composition from hydrolysis and degradation in low-pH environments. The disclosed CNT vaccine compositions are modular systems that allow for flexible addition and subtraction of these elements which allows for exquisite control over many of the variables that are important for optimizing an effective vaccine delivery system. The modular nature of these vaccine compositions allows for libraries of vaccine compositions that may be tested for efficacy for any particular antigen.

1. Antigens

The CNT modular vaccines may contain any suitable antigen or combination of antigens. Exemplary antigens are discussed above with respect to CNT aAPC compositions.

2. Targeting Molecules for Professional Antigen Presenting Cells

Of the main types of antigen-presenting cells (B cell, macrophages and DCs), the DC is the most potent and is responsible for initiating all antigen-specific immune responses. One biological feature of DCs is their ability to sense conditions under which antigen is encountered, initiating a process of DC maturation. Using receptors for various microbial and inflammatory products, DCs respond to antigen exposure in different ways depending on the nature of the pathogen (virus, bacteria, protozoan) encountered. This information is transmitted to T cells by altered patterns of cytokine release at the time of antigen presentation in lymph nodes, altering the type of T cell response elicited. Thus, targeting DCs provides the opportunity not only to quantitatively enhance the delivery of antigen and antigen responses in general, but to qualitatively control the nature of the immune response depending on the desired vaccination outcome.

Dendritic cells express a number of cell surface receptors that can mediate the endocytosis of bound antigen. Targeting exogenous antigens to internalizing surface molecules on systemically-distributed antigen presenting cells facilitates uptake of antigens and thus overcomes a major rate-limiting step in immunization and thus in vaccination.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (Hawiger, et al., J. Exp. Med., 194(6):769-79 (2001); Bonifaz, et al., J. Exp. Med., 196(12):1627-38 (2002); Bonifaz, et al., J. Exp. Med., 199(6):815-24 (2004)). In these experiments, antigens were fused to an anti-DEC205 heavy chain and a recombinant antibody molecule was used for immunization.

A variety of other endocytic receptors, including a mannose-specific lectin (mannose receptor) and IgG Fc receptors, have also been targeted in this way with similar enhancement of antigen presentation efficiency. Other suitable receptors which may be targeted include, but are not limited to, DC-SIGN, 33D1, SIGLEC-H, DCIR, CD11c, heat shock protein receptors and scavenger receptors.

Other receptors which may be targeted include the toll-like receptors (TLRs). TLRs recognize and bind to pathogen-associated molecular patterns (PAMPs). PAMPs target the TLR on the surface of the dendritic cell and signals internally, thereby potentially increasing DC antigen uptake, maturation and T-cell stimulatory capacity. PAMPs conjugated to the particle surface or co-encapsulated include unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

3. Targeting Molecules for Epithelial Cells

The potential efficacy of vaccine systems is determined in part by their route of administration into the body. While injection (intradermal, intramuscular, intravenous) is an acceptable solution in many cases, having a vaccine product that is orally available will greatly extend its ease of use and applicability on a global scale. For orally administered vaccines, epithelial cells constitute the principal barrier that separates an organism's interior from the outside world. Epithelial cells such as those that line the gastrointestinal tract form continuous monolayers that simultaneously confront the extracellular fluid compartment and the extracorporeal space. Uptake of antigen by these gut epithelial cells can be enhanced, and the antigens carried by "transcytosis" to the lymphatics where they have access to dendritic cells.

In one embodiment, modular CNT vaccines may include epithelial cell recognition elements. Epithelial cell targeting molecules include monoclonal or polyclonal antibodies or bioactive fragments thereof that recognize and bind to epitopes displayed on the surface of epithelial cells. Epithelial cell targeting molecules also include ligands which bind to a cell surface receptor on epithelial cells. Ligands include, but are not limited to, molecules such as polypeptides, nucleotides and polysaccharides.

A variety of receptors on epithelial cells may be targeted by epithelial cell targeting molecules. Examples of suitable receptors to be targeted include, but are not limited to, IgE Fc receptors, EpCAM, selected carbohydrate specificites, dipeptidyl peptidase, and E-cadherin.

4. Additional Adjuvants

The modular CNT vaccines may include additional adjuvants. These can be incorporated into, administered with, or administered separately from, the CNT vaccine compositions.

In one embodiment the adjuvant is the synthetic glycolipid alpha-galactosylceramide (αGalCer). Dendritic cells presenting antigens in the context of CD1d can lead to rapid innate and prolonged production of cytokines such as interferon and IL-4 by natural killer T cells (NKT cells). CD1d is a major histocompatibility complex class I-like molecule that presents glycolipid antigens to a subset of NKT cells. Advantageously, αGalCer is not toxic to humans and has been shown to act as an adjuvant, priming both antigen-specific CD4+ and CD8+ T cell responses. For example, it has been shown that αGalCer in conjunction with a malaria vaccine can lead to cytotoxic responses against infected cells, which is an ideal scenario for vaccines against infectious diseases. In addition to αGalCer, other glycolipids that function as adjuvants to activate NKT cell-mediated immune responses can be used.

In another embodiment the adjuvant can be, but is not limited to, one or more of the following: oil emulsions (e.g., Freund's adjuvant); saponin formulations; virosomes and viral-like particles; bacterial and microbial derivatives including, but not limited to carbohydrates such as lipopolysachharide (LPS); immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor; and co-stimulatory molecules, such as those of the B7 family. Such proteinaceous adjuvants may be provided as the full-length polypeptide or an active fragment thereof, or in the form of DNA, such as plasmid DNA 5. Molecules to Inhibit Degradation of CNT Vaccine Compositions in Extreme pH Environments CNT vaccine compositions administered orally will encounter a corrosive environment in the gastrointestinal (GI) tract with areas of low and high pH, as well as resident degradative enzymes and solubilizing agents. For this reason, 'shielding' is a desired feature to protect the vaccine composition in transit to the GI epithelium. In one embodiment, modular CNT vaccine compositions further include pH-sensitive molecules which protect the composition from hydrolysis and degradation in low pH environments. Such pH-sensitive protecting molecules are preferred because subsequent to the transit of the vaccine composition through a low pH environment, upon reaching its destination in the higher pH intestinal site, the CNT vaccine compositions should expose epithelial targeting molecules to allow for specific interactions with target epithelial cells.

Exemplary non-pH-sensitive molecules include, but are not limited to, poly(ethylene) glycol, gelatin and albumins. Exemplary pH-sensitive molecules include, but are not limited to, elastin and poly(methacrylic) acid (PMAA). Both of these molecules are in extended conformations at pH 7.4 and shrink rapidly (within seconds) upon exposure to lower pH environments (below pH 5 for elastin and below pH 5-6 for poly(methacylic) acid). Other exemplary pH-sensitive molecules which may be used include poly(acrylic acid), poly(methyl methacrylic acid) and poly(N-alkyl acrylamides).

E. Pharmaceutically Acceptable Excipients

The CNT compositions may be administered in combination with a physiologically or pharmaceutically acceptable carrier, excipient, or stabilizer. The term "pharmaceutically acceptable" means a non-toxic material that does not interfere with the effectiveness of the biological activity of the active ingredients. The term "pharmaceutically-acceptable carrier" means one or more compatible solid or liquid fillers, dilutants or encapsulating substances which are suitable for administration to a human or other vertebrate animal. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. In the preferred embodiment, administration is by injection. Typical formulations for injection include a carrier such as sterile saline or a phosphate buffered saline. Viscosity modifying agents and preservatives are also frequently added.

Optional pharmaceutically acceptable excipients especially for enteral, topical and mucosal administration, include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (POLYPLASDONE® XL from GAF Chemical Corp).

Stabilizers are used to inhibit or retard decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-b-alanine, sodium N-lauryl-b-iminodipropionate, myristoamphoacetate, lauryl betaine and lauryl sulfobetaine.

If desired, the particles may also contain minor amount of nontoxic auxiliary substances such as wetting or emulsifying agents, dyes, pH buffering agents, or preservatives.

The particles may be complexed with other agents. The pharmaceutical compositions may take the form of, for example, tablets or capsules prepared by conventional means with pharmaceutically acceptable excipients such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the compounds and their physiologically acceptable solvates may be formulated for administration.

Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

The particles may be coated. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Röhm Pharma, Darmstadt, Germany), zein, shellac, and polysaccharides. Additionally, the coating material may contain conventional carriers such as plasticizers, pigments, colorants, glidants, stabilization agents, pore formers and surfactants.

III. Methods of Use

A. T Cell Activation

The CNT aAPC and CNP compositions are useful for activating T cells either in vivo, for active immunotherapy applications, or ex vivo, for adoptive immunotherapy applications. The CNT vaccine compositions are useful for in vivo administration of antigens to professional APCs to elicit T cell activation for prophylactic or therapeutic applications.

The examples below demonstrate that anti-CD3 antibodies adsorbed onto SWNT bundles stimulate cells more efficiently than equivalent concentrations of soluble anti-CD3 antibodies. It is believed that the enhanced activity of CNT aAPCs is due to the large surface area of the CNTs and their unique aspect ratio, as well as their efficient adsorption of a large number of proteins. Furthermore, SWNT bundles bound to anti-CD3 antibodies are more efficient at activating T cells than other high surface area compositions, such as activated carbon and polystyrene and C60 nanoparticles, even when normalized by surface area. This indicates that SWNTs possess unique properties in addition to their high surface area that make them ideally suited to function as scaffolds for aAPCs.

Activation of T cells increases their proliferation, cytokine production, differentiation, effector functions and/or survival. Methods for measuring these are well known to those in the art. The T cells activated by the CNT compositions can be any cell which express the T cell receptor, including α/β and γ/δ T cell receptors. T-cells include all cells which express CD3, including T-cell subsets which also express CD4 and CD8. T-cells include both naive and memory cells and effector cells such as CTL. T-cells also include regulatory cells such as Th1, Tc1, Th2, Tc2, Th3, Treg, and Tr1 cells. T-cells also include NKT-cells and similar unique classes of the T-cell lineage. In preferred embodiments the T cells that are activated are CD8+ T cells.

1. Subjects to be Treated

In general, the CNT compositions are useful for treating a subject having or being predisposed to any disease or disorder to which the subject's immune system mounts an immune response. Treating a disease or disorder to which the subject's immune system mounts an immune response may include inhibiting or delaying the development of the disease or disorder or inhibiting or reducing the symptoms of the disease or disorder. The compositions are useful as prophylactic compositions, which confer resistance in a subject to subsequent tumor development or exposure to infectious agents. The compositions are also useful as therapeutic compositions, which can be used to initiate or enhance a subject's immune response to a pre-existing antigen, such as a tumor antigen in a subject with cancer, or a viral antigen in a subject infected with a virus.

The compositions are also useful to treat or prevent diseases and disorders characterized by undesirable activation, overactivation or inappropriate activation of the immune system, such as occurs during allergic responses, autoimmune diseases and disorders, graft rejection and graft-versus-host-disease. Methods for using CNT aAPCs and CNPs for treatment of these conditions are described in more detail below.

The desired outcome of a prophylactic, therapeutic or de-sensitized immune response may vary according to the disease, according to principles well known in the art. For example, an immune response against an infectious agent may completely prevent colonization and replication of an infectious agent, affecting "sterile immunity" and the absence of any disease symptoms. However, treatment against infectious agents with the CNT compositions may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

a. Subjects Infected with or Exposed to Infectious Agents

In some instances, the subject can be treated prophylactically, such as when there may be a risk of developing disease from an infectious agent. Infectious agents include bacteria, viruses and parasites. An individual traveling to or living in an area of endemic infectious disease may be considered to be at risk and a candidate for prophylactic vaccination against the particular infectious agent. Preventative treatment can be applied to any number of diseases where there is a known relationship between the particular disease and a particular risk factor, such as geographical location or work environment.

b. Subjects with or a Risk of Developing Malignant Tumors

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site. The compositions and method described herein may be useful for treating subjects having malignant tumors. Treating a subject having a malignant tumor includes delaying or inhibiting the growth of a tumor in a subject, reducing the growth or size of the tumor, inhibiting or reducing metastasis of the tumor, and inhibiting or reducing symptoms associated with tumor development or growth.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. A melanoma is a type of carcinoma of the skin for which this technology is particularly useful. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated in with the provided compositions and methods include, but are not limited to, the following: bladder, brain, breast, cervical, colo-rectal, esophageal, kidney, liver, lung, nasopharangeal, pancreatic, prostate, skin, stomach, uterine. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

c. Immunosuppressed Conditions

The CNT compositions may also be used for treatment of disease conditions characterized by immunosuppression, including, but not limited to, AIDS or AIDS-related complex, idiopathic immunosuppression, drug induced immunosuppression, other virally or environmentally-induced conditions, and certain congenital immune deficiencies. The CNT compositions may also be employed to increase immune function that has been impaired by the use of radiotherapy of immunosuppressive drugs (e.g., certain chemotherapeutic agents), and therefore can be particularly useful when used in conjunction with such drugs or radiotherapy.

d. Subjects Exposed to Allergens

The compositions and methods disclosed herein are useful to treat and/or preventing allergic reactions, such as allergic reactions which lead to anaphylaxis. Allergic reactions may be characterized by the $T_H2$ responses against an antigen leading to the presence of IgE antibodies. Stimulation of $T_H1$ immune responses and the production of IgG antibodies may alleviate allergic disease. Thus, the disclosed vaccine compositions may lead to the production of antibodies that prevent and/or attenuate allergic reactions in subjects exposed to allergens. These can be used to enhance blocking or tolerance inducing reactions.

e. Subjects with or at Risk of Developing Autoimmune Diseases or Disorders

The compositions and methods are useful for the treatment or prevention of autoimmune diseases and disorders. Exemplary autoimmune diseases include vasculitis, Wegener's granulomatosis, Addison's disease, alopecia, ankylosing spondylitis, antiphospholipid syndrome, Behcet's disease, celiac disease, chronic fatigue syndrome, Crohn's disease, ulcerative colitis, type I diabetes, fibromyalgia, autoimmune gastritis, Goodpasture syndrome, Graves' disease, idiopathic thrombocytopenic purpura (ITP), lupus, Meniere's multiple sclerosis, myasthenia gravis, pemphigus vulgaris, primary biliary cirrhosis, psoriasis, rheumatoid arthritis, rheumatic fever, sarcoidosis, scleroderma, vitiligo, vasculitis, small vessel vasculitis, hepatitis, primary biliary cirrhosis, rheumatoid arthritis, Chrohn's disease, ulcerative colitis, sarcoidosis, scleroderma, graft versus host disease (acute and chronic), aplastic anemia, and cyclic neutropenia.

f. Subjects Undergoing or at Risk of Graft Rejection or Graft-Versus-Host Disease The compositions and methods are useful for the treatment or prevention of graft rejection or graft versus host disease. The methods and compositions can be used in the prevention or treatment of any type of allograft rejection or graft versus host disease for any type of graft, including a xenograft. The allograft can be an organ transplant, such as, but not limited to, a heart, kidney, liver, lung or pancreas. Alternatively, the allograft can be a tissue transplant, such as, but not limited to, heart valve, endothelial, cornea, eye lens or bone marrow tissue transplant. In yet other embodiments, the allograft can be a skin graft.

B. Adoptive Immunotherapy

The disclosed CNT aAPCs and CNPs are particularly useful to activate T cells ex vivo for adoptive immunotherapy. In adoptive immunotherapy, a source of T cells is obtained from a subject to be treated for use in adoptive immunotherapy in an organism in which an immune response can be elicited, e.g., mammals. Examples of subjects include humans, dogs, cats, mice, rats, and transgenic species thereof, although humans are preferred. T cells can be obtained from a number of sources, including peripheral blood leukocytes, bone marrow, lymph node tissue, spleen tissue, and tumors. In a preferred embodiment, peripheral blood leukocytes are obtained from an individual by leukopheresis. To isolate T cells from peripheral blood leukocytes, it may be necessary to lyse the red blood cells and separate peripheral blood leukocytes from monocytes by, for example, centrifugation through, e.g., a PERCOLL™ gradient.

A specific subpopulation of T cells, such as $CD4^+$ or $CD8^+$ T cells, can be further isolated by positive or negative selection techniques. For example, negative selection of a T cell population can be accomplished with a combination of antibodies directed to surface markers unique to the cells negatively selected. One suitable technique includes cell sorting via negative magnetic immunoadherence, which utilizes a cocktail of monoclonal antibodies directed to cell surface markers present on the cells negatively selected. For example, to isolate $CD4^+$ cells, a monoclonal antibody cocktail typically includes antibodies to CD14, CD20, CD11b, CD16, HLA-DR, and CD8. The process of negative selection results in an essentially homogenous population of the desired T cell population.

CNT aAPCs and CNPs may be customized according to the subject and the condition or disease to be treated. In one embodiment, the CNT aAPCs and CNPs contain at least one polyclonal T cell receptor activator, such as an anti-T cell receptor antibody. Polyclonal T cell activation can be useful because it can expand a T cell population more quickly than antigen-specific methods. The expanded polyclonal T cells can then be sorted to select for T cells with a specificity for the epitopes of interest. In another embodiment, the CNT aAPCs contain MHC class I or MHC class II molecules bound to antigens of interest for antigen-specific T cell activation. The MHC polypeptides used in the CNT aAPCs and CNPs are preferably selected to match the MHC alleles expressed by the subject to be treated. The antigen is selected based on the condition or disease to be treated or prevented. The antigen may be derived from the subject to be treated.

The selected T cells are then contacted in appropriate medium with the CNT aAPCs or CNPs. CNT aAPCs or CNPs are used in amounts effective to cause activation and proliferation of T cells. The T cells are contacted with the CNT aAPCs or CNPs for periods of time necessary for expansion of the T cells. It may be advantageous to maintain long-term culture of a population of T cells following the initial activation and stimulation, by separating the T cells from the stimulus after a period of about 12 to about 14 days. In certain embodiments, it may be desirable to separate the T cells from the stimulus after a period of about 2, 3, 4, 5, 6, 7, 8, 9, 10, or 11 days. In certain embodiments, it may be desirable to separate the T cells from the stimulus after a period of less than one day, such as after about an hour, or 2, 3, 4, 5, 6, 7, 8, 9, 10, 11, 12, 13, 14, 15, 16, 17, 18, 19, 20, 21, 22, or 23 hours. The rate of T cell proliferation is monitored periodically (e.g., daily) by, for example, examining the size or measuring the volume of the T cells, such as with a Coulter Counter. In this regard, a resting T cell has a mean diameter of about 6.8 microns, and upon initial activation and stimulation, in the presence of the stimulating ligand, the T cell mean diameter will increase to over 12 microns by day 4 and begin to decrease by about day 6. The T cells may be stimulated through multiple rounds of activation by the CNT aAPCs or CNPs. For example, when the mean T cell diameter decreases to approximately 8 microns, the T cells may be reactivated and re-stimulated to induce further proliferation of the T cells. Alternatively, the rate of T cell proliferation and time for T cell re-stimulation can be monitored by assaying for the presence of cell surface molecules, such as, CD154, CD54, CD25, CD137, CD134, which are induced on activated T cells.

Following activation and expansion of the T cells, they are administered to the subject in amounts effective to induce an immune response. In some embodiments the T cells are isolated from CNPs prior to administration to the subject, preferably using magnetic separation. The T cells may be administered separately from, or in combination with, the CNT aAPCs or CNPs. The immune response induced in the animal by administering the compositions may include cellular immune responses mediated by $CD8^+$ T cells, capable of killing tumor and infected cells, and $CD4^+$ T cell responses. Humoral immune responses, mediated primarily by B cells that produce antibodies following activation by $CD4^+$ T cells, may also be induced. In a preferred embodiment, the immune response is mediated by cytolytic $CD8^+$ T cells. A variety of techniques which are well known in the art may be used for analyzing the type of immune responses induced by the compositions and methods disclosed herein (Coligan et al., *Current Protocols in Immunology*, John Wiley & Sons Inc. (1994)).

1. Adoptive Immunotherapy of Autoimmune Diseases and Disorders, Allergic Reactions, Graft Rejection and Graft-Versus-Host-Disease Adoptive immunotherapy may also be used to treat or prevent conditions associated with undesirable activation, over-activation or inappropriate or aberrant activation of an immune response, as occurs in conditions including autoimmune disorders and diseases, allergic reactions, graft rejection and graft-versus-host disease. In one embodiment, undesirable or aberrant antigen-specific immune responses are treated or prevented by adoptive immunotherapy using "regulatory" T cells (Tregs) activated by the compositions and methods disclosed herein.

Immunological self-tolerance is critical for the prevention of autoimmunity and maintenance of immune homeostasis. The ability of the immune system to discriminate between self and non-self is controlled by mechanisms of central and peripheral tolerance. Central tolerance involves deletion of self-reactive T lymphocytes in the thymus at an early stage of development (Rocha, et al., *Science*, 251:1225-1228 (1991); Kisielow, et al., *Nature*, 333:742-746 (1988)). Several mechanisms of peripheral tolerance have been described, including T cell anergy and ignorance (Schwartz, *Science*, 248:1349-1356 (1990); Miller, et al., *Immunol. Rev.*, 133:131-150 (1993)). Studies have provided firm evidence for the existence of a unique $CD4^+CD25^+$ population of professional regulatory/suppressor T cells that actively and dominantly prevent both the activation as well as the effector function of autoreactive T cells that have escaped other mechanisms of tolerance (Sakaguchi, et al., *J. Immunol.*, 155:1151-1164 (1995); Takahashi, et al., *Int. Immunol.*, 10:1969-1980 (1998); Itoh, et al., *J. Immunol.*, 162:5317-5326 (1999)). The elimination or inactivation of these cells resulted in severe autoimmune disease, and was also found to enhance immune responses to alloantigens and even tumors (Sakaguchi, et al., *J. Immunol.*, 155:1151-1164 (1995); Itoh, et al., *J. Immunol.*, 162:5317-5326 (1999); Shimizu, et al., *J. Immunol.*, 163:5211-5218 (1999)). Autoantigen-specific regulatory T (Treg) cells actively regulate autoimmunity and induce long term tolerance and have application as a strategy for inducing long-lived tolerance.

T cells are obtained from the subject to be treated as described above, and a Treg enriched cell population is obtained by negative and or positive selection. An autoantigen-specific regulatory T (Treg) cell enriched composition is one in which the percentage of autoantigen-specific Treg cells is higher than the percentage of autoantigen-specific Treg cells in the originally obtained population of cells. In particular embodiments, at least 75%, 85%, 90%, 95%, or 98% of said cells of the composition are autoantigen-specific regulatory T cells. To maximize efficacy, the subpopulation is enriched to at least 90%, preferably at least 95%, and more preferably at least 98% Treg cells, preferably $CD4^+CD25^+CD62L^+$ Treg cells. Positive selection may be combined with negative selection against cells comprising surface makers specific to non-Treg cell types, such as depletion of CD8, CD11b, CD16, CD19, CD36 and CD56-bearing cells.

The Treg cells are activated in a polyclonal or antigen-specific manner ex vivo using the compositions, as described above, expanded, and administered to the subject to be treated. In another embodiment, a population of T cells not enriched for Treg cells is activated and expanded, and the Treg cells are selected from the expanded T cell population using appropriate positive and/or negative selection.

Adoptive immunotherapy using Treg cells can be used for prophylactic and therapeutic applications. In prophylactic applications, Treg cells are administered in amounts effective to eliminate or reduce the risk or delay the outset of conditions associated with undesirable activation, over-activation or inappropriate or aberrant activation of an immune response, including physiological, biochemical, histologic and/or behavioral symptoms of the disorder, its complications and intermediate pathological phenotypes presenting during development of the disease or disorder. In therapeutic applications, the compositions and methods disclosed herein are administered to a patient suspected of, or already suffering from such a condition associated with undesirable activation, over-activation or inappropriate or aberrant activation of an immune response to treat, at least partially, the symptoms of the disease (physiological, biochemical, histologic and/or behavioral), including its complications and intermediate pathological phenotypes in development of the disease or disorder. An amount adequate to accomplish therapeutic or prophylactic treatment is defined as a therapeutically- or prophylactically-effective amount.

With respect to allograft rejection or graft versus host disease, in a preferred embodiment, adoptive immunotherapy with Treg cells is initiated prior to transplantation of the allograft. In certain embodiments, the Treg cells can be administered to the subject for a day, three days, a week, two weeks or a month prior to a transplantation. In other embodiments, the Treg cells are administered for a week, two weeks, three weeks, one month, two months, three months or six months following a transplantation. In a preferred embodiment, Treg cells are administered both before and after a transplantation is carried out.

The outcome of the therapeutic and prophylactic methods disclosed herein is to at least produce in a patient a healthful benefit, which includes, but is not limited to, prolonging the lifespan of a patient, delaying the onset of one or more symptoms of the disorder, and/or alleviating a symptom of the disorder after onset of a symptom of the disorder. For example, in the context of allograft rejection, the therapeutic and prophylactic methods can result in prolonging the lifespan of an allograft recipient, prolonging the duration of allograft tolerance prior to rejection, and/or alleviating a symptom associated with allograft rejection.

In another embodiment, undesirable or aberrant antigen-specific immune responses are treated or prevented by adoptive immunotherapy by using the compositions to activate and expand T cells specific for IgE or CD40L.

Immune responses to foreign, sometimes innocuous, substances such as pollen, dust mites, food antigens and bee sting can result in allergic diseases such as hay fever, asthma and systemic anaphylaxis Immune responses to self-antigens such as pancreatic islet antigens and cartilage antigens can lead to diabetes and arthritis, respectively. The hallmark of the allergic diseases is activation of $CD4^+$ T cells and high production of IgE by B cells, whereas the salient feature of autoimmune diseases are activation of $CD4^+$ T cells and over production of inflammation cytokines. Activated $CD4^+$ T cells transiently express the self antigen CD40L.

Cytotoxic T lymphocytes (CTLs) specific for antigenic peptides derived from IgE molecule can be generated ex vivo using the artificial antigen presenting cells and methods disclosed herein presenting antigenic IgE peptides. These IgE specific CTLs can be administered to a subject to lyse the target cells loaded with IgE peptides and inhibit antigen specific IgE responses in vivo. These IgE specific CTLs can also be used to prevent or treat the development of lung inflammation and airway hypersensitivity.

Similarly, cytotoxic T lymphocytes (CTLs) specific for antigenic peptides derived from CD40L can be generated ex vivo using the artificial antigen presenting cells and methods disclosed herein presenting antigenic CD40L peptides. These CD40L specific CTLs can be administered to a subject to lyse target activated CD4+ cells in vivo. These CD40L specific CTLs can be used to inhibit CD4-dependent antibody responses of all isotypes in vivo.

C. Active Immunotherapy

The CNT aAPCs, CNPs, and vaccine compositions may also be used for active immunotherapy. For active immunotherapy, the CNT aAPCs, CNPs, or CNT vaccine compositions are administered directly to the subject to be treated. In general, methods of administering vaccines are well known in the art. Any acceptable method known to one of ordinary skill in the art may be used to administer a formulation to the subject. The administration may be localized (i.e., to a particular region, physiological system, tissue, organ, or cell type) or systemic. CNT aAPCs, CNPs, or CNT vaccine compositions may be administered by a number of routes including, but not limited to, injection: intravenous, intraperitoneal, intramuscular, or subcutaneous, to a mucosal surface (oral, sublingual or buccal, nasal, rectal, vaginal, pulmonary), or transdermal. In some embodiments, the injections can be given at multiple locations. The CNT aAPCs, CNPs, or CNT vaccine compositions can also be administered directly to an appropriate lymphoid tissue, such as the spleen, lymph nodes or mucosal-associated lymphoid tissue.

The CNT vaccine compositions are particularly suitable for enteral administration. The ability to target vaccine compositions to epithelial cells in the digestive tract greatly facilitates the ability of a vaccine to induce mucosal and systemic immunity when administered orally. Molecules, as described above, which protect the vaccine composition and its constituents from hydrolysis and degradation in low pH environments also enhance the efficacy of vaccines administered orally.

Administration of the formulations may be accomplished by any acceptable method which allows an effective amount of the CNT aAPCs, CNPs, or CNT vaccine compositions to reach their target. The particular mode selected will depend upon factors such as the particular formulation, the severity of the state of the subject being treated, and the dosage required to induce an effective immune response. As generally used herein, an "effective amount" is that amount which is able to induce an immune response in the treated subject. The actual effective amounts of compositions can vary according to factors including the specific antigen or combination thereof being utilized, the density and/or nature of the associated co-stimulatory molecules, the release characteristics of, the particular composition formulated, the mode of administration, and the age, weight, condition of the subject being treated, as well as the route of administration and the disease or disorder.

EXAMPLES

Example 1. Effect of Chemical Treatments on Surface Area of SWNTs and Protein Adsorption Materials and Methods:
Materials Biotin Anti-CD3 was purchased from BD Biosciences— Pharminogen (San Jose, Calif.). Treated and raw SWNT were obtained from the Department of Chemical Engineering at Yale University.

Raw SWNT Chemical Treatment

SWNT bundles were stirred in a 3M $HNO_3$ at 70° C. for 1 hour. The sample was then filtered through a 5 μm pore size PTFE membrane and dried at 45° C. overnight in an oven. Reduced samples entailed the addition of $LiBH_4$ solution in THF (200 mg SWNT+125 ml THF+400 mg $LiBH_4$), then sonication for 1.5 hour. This chemical procedure gives the (3M $HNO_3/LiBH_4$) SWNT group. If the procedure was stopped after the oxidation step (without $LiBH_4$ treatment), the SWNT group is simply called (3M $HNO_3$).

Determination of Dry SWNT Surface Area

Dry SWNT (or A.C.) surface area was determined by physisorption of nitrogen using the Brunauer-Emmett-Teller method (B.E.T). SWNT (or A.C.) physisorption and estimation of surface area were performed using an Autosorb-1 from Quantachrome.

Transmission Electron Microscopy (TEM)

TEM images were obtained using a Philips Tecnai F12 TEM instrument. One mg of pre-weighed SWNT (or A.C) was mixed in 10 ml of ethanol (ACS/USP grade), and dispersed by ultra-sonication. A droplet of the SWNT/ethanol (or A.C./ethanol) suspension was then applied on a holey carbon coated copper TEM grid before air-drying.

Scanning Electron Microscopy (SEM)

SEM images were obtained on a XL-30 ESEM-FEG microscope from FEI Company. One hundred micrograms per milliliter of SWNT (or A.C.) solution dissolved in PBS was washed and resuspended in dionized water. The washing step was repeated three times using a micro-centrifuge at 12,000 rpm for 8 minutes. Ten microliters of the washed solution was applied to 0.25 $cm^2$ of carbon tape mounted on an aluminum stub. The stub is placed at −80° C. for 2 hours and then lyophilized overnight using a Labonco Free Zone 1 Lyophilizer (vacuum at 0.057 mBar, −44° C. collector).

SWNT Sterilization for Cellular Studies

A known amount of SWNT was dissolved in dionized water then heated in a vacuum oven at 180° C. The SWNT sample was next sonicated in a known volume of sterile phosphate buffer solution (PBS) for 10 minutes then exposed to ultraviolet light for 20 minutes. The same procedure was applied to activated carbon and C60 samples. PS samples were sterilized using a 0.45 um MILLEX®HA sterile filter unit (MF-Millipore MCE membrane), dissolved in sterile PBS, then exposed to ultraviolet light for 20 minutes.

Adsorption of BSA onto SWNT

Bovine Serum Albumin (40 kDa) was selected as a model protein to quantify physical adsorption onto SWNT of known dry SWNT surface area. A sample obtained from a sterile stock of SWNT was dissolved in PBS to a concentration of 300 ng/ml then sonicated for 10 minutes to obtain uniform dispersion. BSA at 600 ng/ml was serially diluted at 200 μl in 1×PBS. The SWNT sample was then dispensed at an equal volume of 200 μl into the prepared BSA samples. The mixture was allowed to mix in a rotary shaker at 4° C. overnight. SWNT mixtures were then centrifuged in a micro-centrifuge at 12,000 rpm for 20 minutes. The supernatant was removed and analyzed for protein content using the BCA and the micro-BCA assays. The amount of BSA loaded onto SWNT was deduced from a simple mass balance based on the difference in protein concentration before and after SWNT addition.

Results:

The tunability of protein adsorption on SWNT through chemical treatment, which may affect surface area for available protein interaction, was first examined. Protein adsorption isotherms were compared from untreated SWNTs, SWNTs treated with a 3M nitric acid (3M $HNO_3$), and SWNTs treated with 3M nitric acid then reduced in lithium borohydride (3M $HNO_3/LiBH_4$). These treatments were chosen because refluxing SWNTs in nitric acid introduces carboxylic acid groups at the open ends leading to sites of defects and hence enhancing capacity for protein adsorption (Hu, et al., *Jour. Phys. Chem. B*, 107:13838-42 (2003)). A second step involving the reduction of the carboxylic groups in lithium borohydride will preferentially reduce the oxygenated groups created by previous acid treatment favoring the dispersion of SWNTs in solution (U.S. Published Application 2004/0232073) and further increasing surface area available for protein adsorption.

Untreated and chemically treated SWNTs were examined at high magnification under transmission electron microscopy (TEM). Aggregated nanotube structures consistent with the bundling morphology were observed. The three groups of SWNTs showed similar structural integrity although some differences were noted. First, the surface of nitric acid treated SWNT appeared to be slightly damaged when compared to untreated SWNT, and can be correlated with the observed increase in the bundle surface area as measured by physiosorption (Hemraj-Benny, et al., *Jour. Coll. Interf. Sci.*, 317(2):375-82 (2008); Cinke, et al., *Chem. Phys. Lett.*, 365:69-74 (2002)). Second, the nitric acid treatment appeared to reduce the amount of impurities, such as remaining catalysts present along with the nanotubes (Hu, et al., *Jour. Phys. Chem. B*, 107:13838-42 (2003); Hemraj-Benny, et al., *Jour. Coll. Interf. Sci.*, 317(2):375-82 (2008); Cinke, et al., *Chem. Phys. Lett.*, 365:69-74 (2002); Park, et al., *Journ. Mater. Chem.*, 16:141-54 (2006)) as seen by the reduction of metallic particles in the TEM images. This purification step may play an important role in rendering the SWNT cytocompatible. The described chemical treatments do not induce gross morphological changes to the SWNT bundles. All three groups appeared as porous curved surfaces under scanning electron microscopy, with crevices on the length scale of cells, which may facilitate cellular interactions.

To ascertain the effect of these treatments on the surface area of the bundles, surface area was estimated using nitrogen physisorption (Hemraj-Benny, et al., *Jour. Coll. Interf. Sci.*, 317(2):375-82 (2008); Cinke, et al., *Chem. Phys. Lett.*, 365:69-74 (2002); Thommes, et al., *Langmuir*, 22:756-64 (2006)). As expected, the surface areas derived from FIG. 5 using Brunauer-Emmett-Teller (B.E.T) analysis, and summarized in Table 1, changed with the associated chemical treatment.

TABLE 1

Surface area of untreated and treated SWNTs

| SWNT Group | Area ($m^2/g$) |
| --- | --- |
| Untreated | 845 |
| 3M $HNO_3$ | 1190 |
| 3M $HNO_3/LiBH_4$ | 1560 |

Untreated SWNTs have the least surface area at 845 $m^2/g$. SWNTs treated with 3M $HNO_3$ produced a surface area of 1190 $m^2/g$. Finally, SWNTs treated with 3M $HNO_3/LiBH_4$ produced the largest increase in surface area at 1560 $m^2/g$. The reduction step with $LiBH_4$ that follows the 3M $HNO_3$ treatment may also play a role in enhancing SWNT surface area further through de-bundling (Liang, et al., *Nano Lett.*, 4:1257-60 (2004)), although such a mechanism is not completely understood.

Figure 6:
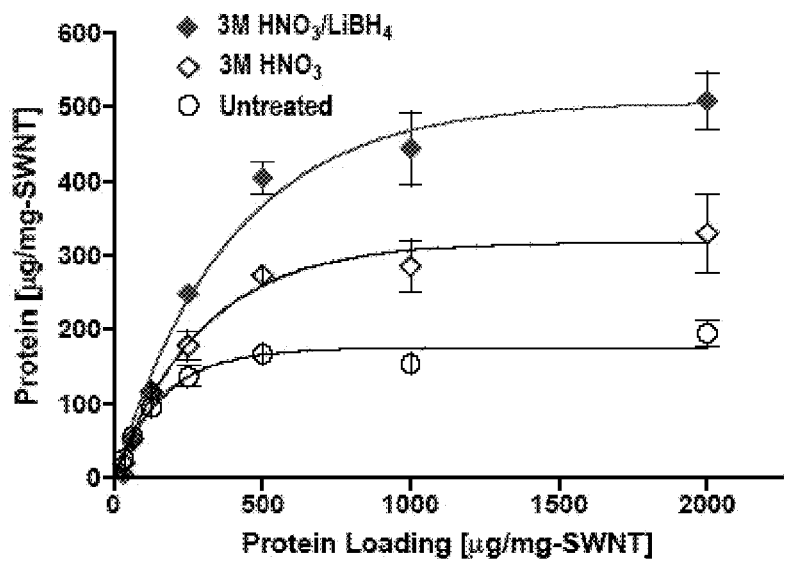
FIG. 6 is a line graph showing the amount of adsorption of a model protein, bovine serum albumin (BSA), to SWNTs that were either untreated (-○-), treated with $HNO_3$ (-◇-), or treated with $HNO_3$ and then $LiBH_4$ (-♦-). The data are presented as the amount of BSA loaded onto SWNTs (μg BSA/mg SWNT) as a function of the amount of BSA added to the SWNTs (μg BSA/mg SWNT).

To assess the effects of chemical treatment of SWNT bundles on protein adsorption, treated and untreated SWNTs were incubated with a model protein, bovine serum albumin (BSA) and measured the respective adsorption isotherms. Results are shown in FIG. 6. The adsorption curves show a correlation between the type of chemical treatment and maximal protein adsorption. SWNTs treated with 3M $HNO_3/LiBH_4$ produced the highest measured surface area and subsequent higher protein adsorption. Thus, this treatment was selected for further studies on T cell stimulation.

Example 2. Cytocompatibility of SWNTs

Figure 7:
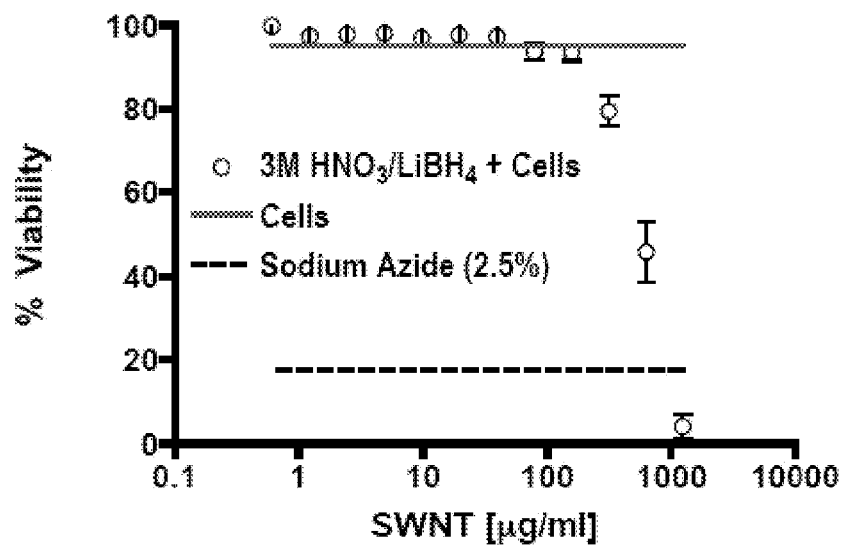
FIG. 7 is a line graph showing the viability of T cells that were either untreated or incubated with 2.5% sodium azide or increasing concentrations of SWNTs. Data are expressed as the percent viability of the T cells as a function of the concentration of added SWNTs.

Materials and methods were as described above with respect to Example 1, except as noted below.
Materials and Methods:
Cytotoxicity Study A metabolic assay, Cell Titer Blue (CTB) assay, was used to assess cell viability exposed to SWNT. Each group was cultured in triplicates. A measured amount of sterile SWNT at 2.5 mg/ml was serially diluted in a sterile 96 well U-bottom cell culture plate with RPMI 1640 containing 10% fetal bovine serum (FBS) and 2% penicillin streptomycin (PS). Sodium azide was included as a negative control at an initial volume of 2.5% and was diluted analogously. Hybridoma T cells (B3Z) at a concentration of $4 \times 10^5$ cells/ml were then added uniformly to the assay. The plate was incubated for 24 hours at 37° C. and 5% $CO_2$. Forty microliters of CTB proliferation reagent was added to each well, including the control (no SWNT) then incubation was allowed for 4 more hours at 37° C. and 5% $CO_2$. Cell proliferation was monitored with the use of cellular standard of known cell population. Fluorescence was recorded at an excitation of 560 nm and emission of 590 nm using a Spectra Max M5 spectrometer from Molecular Devices (Sunnyvale, Calif.).
Results:

The cytocompatibility of SWNTs modified with 3M $HNO_3/LiBH_4$ on T cells was examined next. SWNTs from this treatment group were titrated and incubated with T cells for 24 hours before comparison to a cytotoxic control, sodium azide. It was observed that treated SWNT did not present any significant toxic effects on T cells below a concentration of 150 µg/ml (FIG. 7). This minimal toxic effect observed with the treated nanotubes was not unexpected since the overall length scale of SWNT bundles for cellular interaction is significantly larger than other reports which support SWNT toxicity Magrez, et al., *Nano Lett.*, 6:1121-5 (2006); Porter, et al., *Nature*, 2:713-7 (2007)). In these reports, single tubes (significantly smaller then bundles) may be internalized causing the observed toxic effects. Thus, internalization of SWNT by T cells is improbable as length of bundles is on the order of hundreds of nanometers to microns. A second possible reason for the observed minimal toxicity is the fact that chemical treatment of SWNTs dissolves the majority of remaining impurities and metal catalysts from previous reactions. This step could provide an improved environment for the proliferation of cells Porter, et al., *Nature*, 2:713-7 (2007); Shvedova, et al., *Jour. Tox. Env. Hlth. Pt. A*, 66(20):1909-26 (2003)). Also, the time scale needed for appropriate activation of T cells is significantly shorter than most time scales involved in reported toxicity results. Finally, the relatively high solubility of 3M $HNO_3/LiBH_4$ SWNTs in water could play a role in enhancing cytocompatibility (Dumortier, et al., *Nano Lett.*, 6:1522-8 (2006)).

Example 3. Stimulation of T Cells Using SWNTs

Materials and methods were as described above with respect to Examples 1 and 2, except as noted below.
Materials and Methods:
T-Cell Stimulation Using Anti CD3 Loaded SWNT The stimulation of T-cells (B3z) was quantified using a mouse IL-2 ELISA. Anti-CD3 and SWNT bundles were mixed overnight at 4° C. on a rotary mixer to allow for physical adsorption of anti-CD3, followed by a washing step to remove unbound anti-CD3. The washed sample was then re-suspended in sterile PBS at the same initial volume. SWNT antibody solution was serially diluted in a microplate followed by the addition of 100 µl of T-Cells (B3z) at $4 \times 10^5$ cells/ml. The cell culture plate was incubated for 24 hrs. at 37° C. and 5% $CO_2$. An identical protocol was used for all SWNT groups. For control, soluble and plated anti-CD3, the stimulus was used in similar amounts to anti CD3 loaded SWNT before the wash step. After incubation an ELISA was then performed on IL-2 extracted from the supernatant of each well to quantify the stimulation of T cells.

Fluorescence Imaging of T-Cell Stimulation Using Anti-CD3 Loaded SWNT

Cells were labeled with carboxyfluorescein diacetate-succinimide ester (CFDA-SE) according to established protocols (Invitrogen-Molecular probes). 1 µl of CFDA-SE was added to cells for 15 minutes at 37° C. and 5% $CO_2$. Cells were then centrifuged and washed 3× in cold 1×PBS. Stained cells were washed once with PBS then added in along with anti CD3 loaded SWNT for stimulation (as described). Imaging was performed using an Olympus IX71 microscope and QICAM 32-0030C-152 camera from QImaging.

Figure 8:
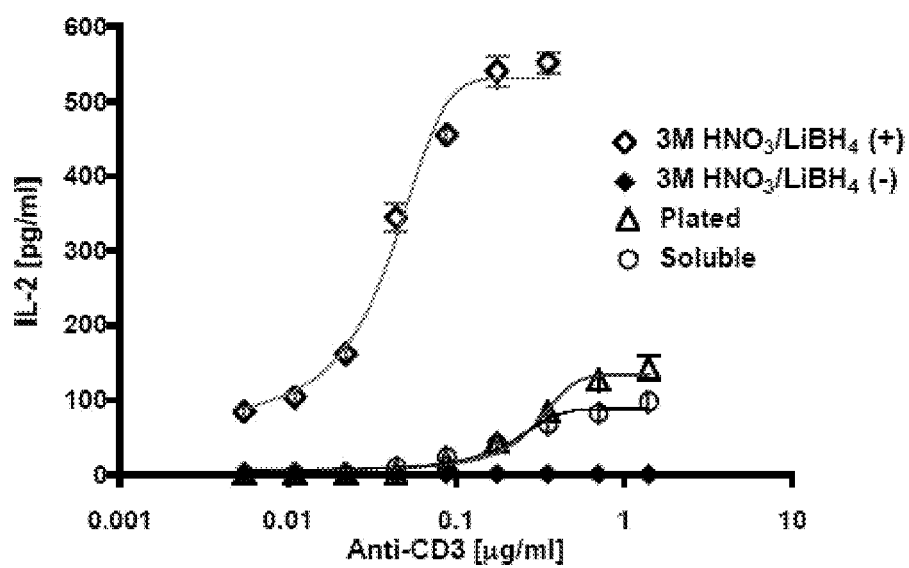
FIG. 8 is a line graph showing the activation of T cells by various stimuli. T cells were activated either by $HNO_3$/$LiBH_4$ treated SWNTs with adsorbed anti-CD3 (-◇-), plate-bound anti-CD3 (-△-), soluble anti-CD3 (-○-), or blank $HNO_3$/$LiBH_4$ treated SWNTs (-♦-). T cell activation was determined by measuring the secretion of IL-2 and data are expressed as the amount of IL-2 secreted (pg/ml) as a function of the concentration of added anti-CD3 (μg/ml).

Results:

Stimulation of T cells using anti-CD3 adsorbed onto 3M $HNO_3$/$LiBH_4$ SWNT was investigated and compared this stimulation to anti-CD3 immobilized on tissue culture plate or free in solution. SWNT bundles incorporating the anti-CD3 stimulus had a dramatic effect on T cell activation as measured by the release of IL-2 (FIG. 8). Activation with antibody immobilized on SWNT was at least four-fold and six-fold greater in comparison to plate-bound antibodies and soluble antibodies respectively. This was consistent with a model concentration-response fit which suggested that the concentration of antibody at which half-maximal T cell stimulation takes place was significantly lower for antibody-SWNT combinations versus plate bound or soluble antibody (Table 2).

TABLE 2

LOG [EC50] for T cell stimulation by various compositions

Figure 9:
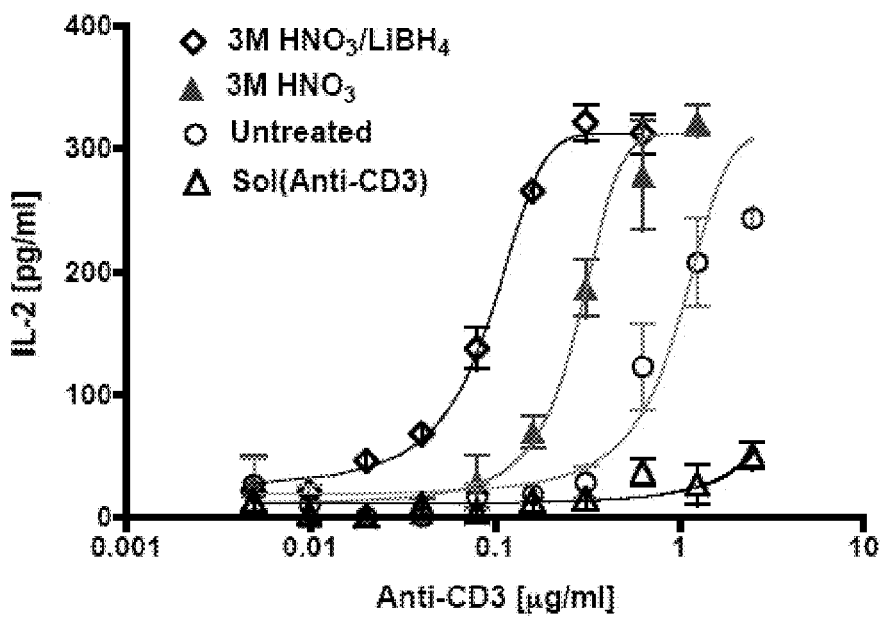
FIG. 9 is a line graph showing the activation of T cells by various stimuli. T cells were activated either by soluble anti-CD3 (-△-) or by anti-CD3 adsorbed onto 3 M $HNO_3$/$LiBH_4$ treated SWNTs (-◇-), 3 M $HNO_3$ treated SWNTs (-▲-) or untreated SWNTs. T cell activation was determined by measuring the secretion of IL-2 and data are expressed as the amount of IL-2 secreted (pg/ml) as a function of the concentration of added anti-CD3 (μg/ml).
Figure 10:
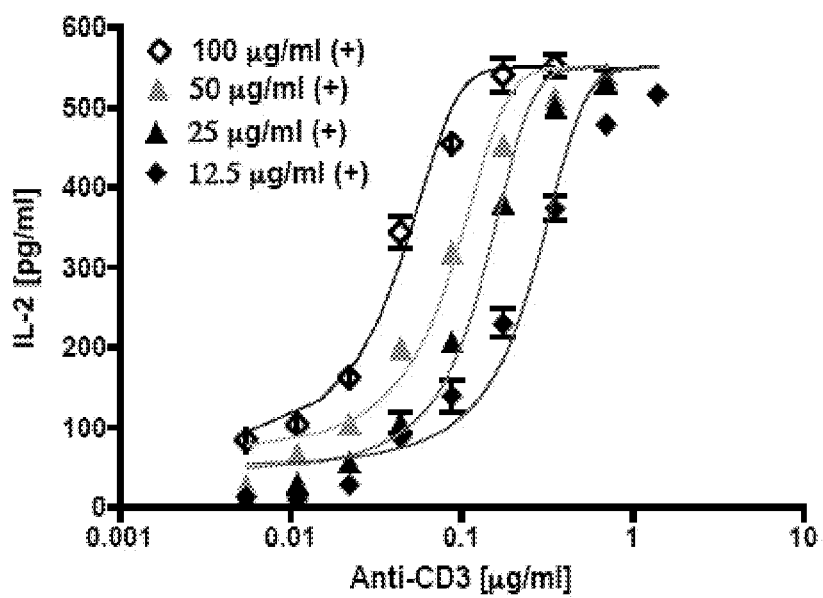
FIG. 10 is a line graph showing the activation of T cells by various stimuli. T cells were activated either by anti-CD3-adsorbed at 100 μg/ml (-◇-), 50 μg/ml (-▲-), 25 μg/ml (-▲-) or 12.5 μg/ml (-♦-). All groups were treated with the same amount of anti-CD3 during adsorption. T cell activation was determined by measuring the secretion of IL-2 and data are expressed as the amount of IL-2 secreted (pg/ml) as a function of the concentration of added anti-CD3 (µg/ml).
Figure 11:
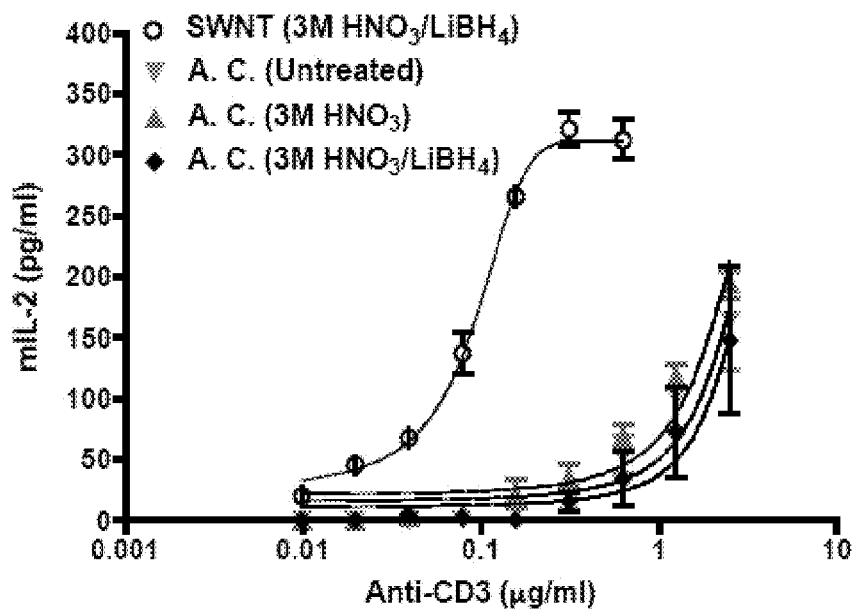
FIG. 11 is a line graph showing the activation of T cells by various stimuli. T cells were activated by anti-CD3-adsorbed adsorbed onto either 3 M $HNO_3$/$LiBH_4$ treated SWNTs (-○-), untreated activated carbon (A.C.) (-▼-), 3 M $HNO_3$ treated A.C. (-▲-), or 3 M $HNO_3$/$LiBH_4$ treated A.C. (-◆-). All materials were used at a concentration of 50 µg/ml, and initially loaded with the same concentration of anti-CD3. T cell activation was determined by measuring the secretion of IL-2 and data are expressed as the amount of IL-2 secreted (pg/ml) as a function of the concentration of added anti-CD3 (µg/ml).
Figure 12:
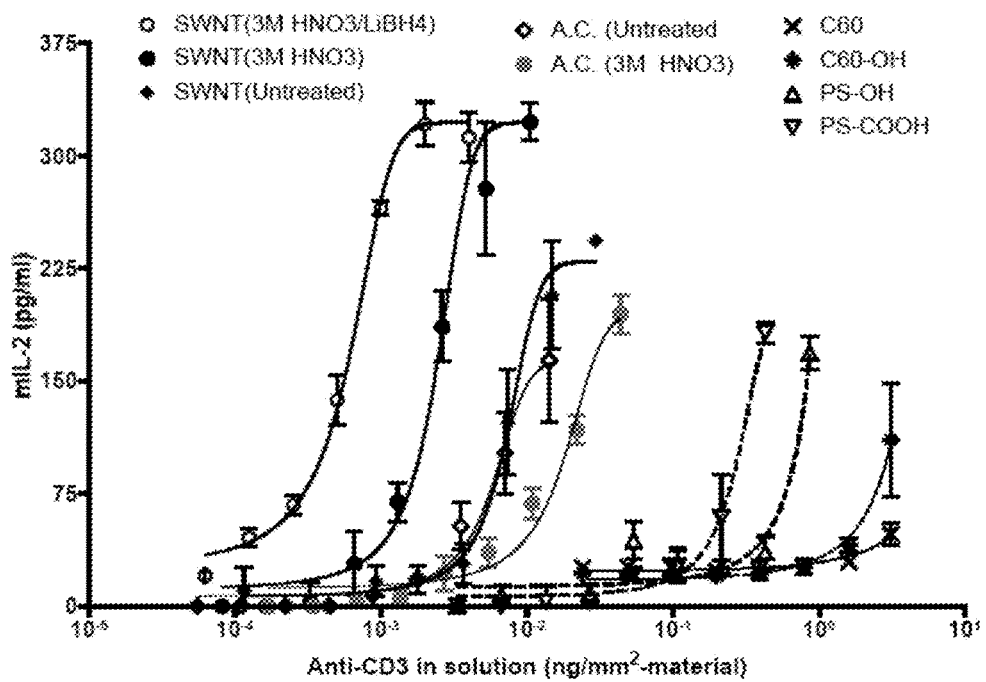
FIG. 12 is a line graph showing the activation of T cells by multiple high surface area materials. T cells were activated by anti-CD3 adsorbed onto either 3 M $HNO_3$/$LiBH_4$ treated SWNTs (-○-), 3 M $HNO_3$ treated SWNTs (-●-), untreated SWNTs (-◆-), untreated A.C. (-◇-), 3 M $HNO_3$ treated A.C. (-⁕-), C60 nanoparticles (-X-), hydroxylated C60 nanoparticles (C60-OH) (-*-), hydroxylated 200 nm polystyrene (PS) beads (PS-OH) (-Δ-), or carboxylated 200 nm PS beads PS-COOH (-∇-). T cell activation was determined by measuring the secretion of IL-2 and data are expressed as the amount of IL-2 secreted (pg/ml) as a function of the concentration of added anti-CD3 (µg/ml) normalized to the antibody per material surface area.

| | | LOG [EC50] | R-squared |
|---|---|---|---|
| FIG. 8 | 3M $HNO_3$/$LiBH_4$ (+) | 0.036 ± 0.002 | 0.977 |
| | PB (anti-CD3) | 0.295 ± 0.020 | 0.952 |
| | Sol (anti-CD3) | 0.213 ± 0.201 | 0.937 |
| FIG. 9 | 3M $HNO_3$/$LiBH_4$ | 0.090 ± 0.002 | 0.981 |
| | 3M $HNO_3$ | 0.278 ± 0.019 | 0.929 |
| | Untreated | 0.973 ± 0.081 | 0.830 |
| | Sol (anti-CD3) | N/A | N/A |
| FIG. 10 | 100 µg/ml (+) | 0.039 ± 0.002 | 0.975 |
| | 50 µg/ml (+) | 0.080 ± 0.004 | 0.971 |
| | 25 µg/ml (+) | 0.128 ± 0.005 | 0.979 |
| | 12.5 µg/ml (+) | 0.250 ± 0.015 | 0.951 |
| FIG. 11 | SWNT (3M $HNO_3$/$LiBH_4$) | 0.088 ± 0.004 | 0.980 |
| | A.C. (untreated) | 2.286 ± 0.165 | 0.735 |
| | A.C. (3M $HNO_3$) | 1.945 ± 0.104 | 0.876 |
| | A.C. (3M $HNO_3$/$LiBH_4$) | N/A | N/A |
| FIG. 12 | SWNT (3M $HNO_3$/$LiBH_4$) | 5.904E-4 ± 0.001 | 0.980 |
| | SWNT (3M $HNO_3$) | 2.242E-3 ± 0.001 | 0.931 |
| | SWNT (untreated) | 7.285E-3 ± 0.001 | 0.913 |
| | A.C. (untreated) | 5.830E-3 ± 0.001 | 0.816 |
| | A.C. (3M $HNO_3$) | 0.0178 ± 0.001 | 0.939 |
| | PS-OH | 2.091 ± 15.980 | 0.889 |
| | PS-COOH | 0.291 ± 0.061 | 0.906 |
| | C60 | N/A | N/A |
| | C60-OH | N/A | N/A |

It was hypothesized that the enhanced stimulation is due to cellular aggregation on the SWNT-stimulus system. Preferential aggregation of T cells onto 3M $HNO_3$/$LiBH_4$ SWNT during stimulation was confirmed qualitatively by comparing the cellular proliferation of fluorescently labeled T cells around anti-CD3 immobilized on SWNT versus blank SWNT. In these images, selective aggregation of T cells was observed around anti-CD3 adsorbed onto 3M $HNO_3$/$LiBH_4$ SWNT scaffolds when compared to 3M $HNO_3$/$LiBH_4$ SWNT alone.

Figure 5:
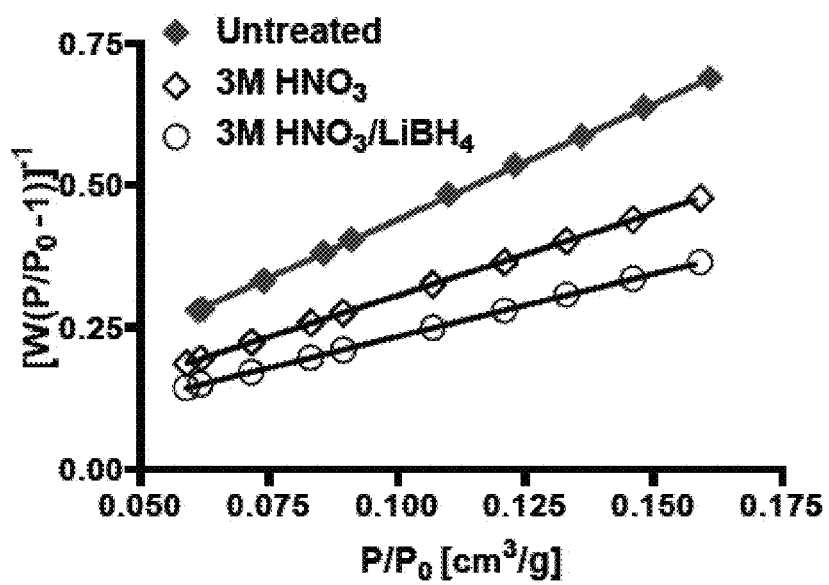
FIG. 5 is a line graph showing the total surface area of SWNTs that were either untreated (-♦-), treated with $HNO_3$ (-◇-), or treated with $HNO_3$ and then $LiBH_4$ (-○-). Total surface area was estimated using nitrogen physisorption and Brunauer-Emmett-Teller analysis. Data are presented as the quantity of adsorbed gas as a function of the ratio of equilibrium to saturation pressure.

To determine the effect of surface treatment on antibody adsorption and levels of T cell stimulation, anti-CD3 adsorbed onto treated and untreated SWNT bundles was incubated with lymphocytes and T cell activation was measured (FIG. 9). The response observed in 3M $HNO_3$/$LiBH_4$ SWNT was more pronounced than other SWNT groups. Modeling parameters from Table 2 show that half maximal stimulation correlated with this observation. The Log [EC50] value for 3M $HNO_3$/$LiBH_4$ SWNT was the smallest (0.090) when compared to other groups (0.278 for 3M $HNO_3$ and 0.973 for untreated). Chemical treatments alter surface functional groups as well as increase the surface area of SWNT bundles (FIG. 5). T cell activation by antibody adsorbed to functionalized 200 nm polystyrene nanoparticles (PS) indicates however that T cell stimulation is not affected by altering surface chemistry from carboxylate groups (mimicking 3M $HNO_3$ treatment) or hydroxyl groups ($LiBH_4$ reduction after oxidation). Thus, the vast surface area of 3M $HNO_3$/$LiBH_4$-treated SWNT bundles is primarily responsible for the observed increase in T cell stimulation. Additionally, these data demonstrate that chemical treatment can be used to tune the extent of protein adsorption and, in turn, to control the degree of T cell stimulation.

Levels of T cell stimulation can be modulated by varying the concentration of SWNT stimulus bundles and keeping the amount of anti-CD3 constant during pre-treatment (FIG. 10). T cells stimulated with SWNT bundles were responsive to the density of SWNT in a concentration-dependent manner. Model fits from Table 2 show a correlation between the SWNT concentration and the half-maximal T cell response. This indicates that overall contact area facilitating a high density of antigen-presentation is a determinant factor for the observed efficiency of SWNT-stimuli on T cell stimulation.

Example 4. Comparison of SWNTs and Other High Surface Area Materials for T Cell Activation Materials and Methods:

Materials and methods were as described above with respect to Examples 1-3, except as noted below.

Surface Area Calculation of PS Beads

Particle count for both PS—OH and PS—COOH is $5.68 \times 10^{12}$ particles/ml (Polysciences Inc.). The particle diameter is 200 nm in both groups. The overall area for presentation was estimated at $2.9 \times 10^{-3}$ $m^2$ (or 29 $m^2$/g) for both PS groups.

Results:

To further investigate the effect of the SWNT surface area on T cell activation, the stimulation potential of other high surface area materials after antibody adsorption was studied. Stimulation by activated carbon (A.C.) (1762 $m^2$/g) was first compared because of the similarity of this material to SWNT bundles. The surface area of the activated carbon was increased with SWNT bundles, but 3M $HNO_3$ treatment resulted in a reduction (Nyogi, et al., Acc. Chem. Res., 35(12):1105-13 (2002)) of the overall surface area (down to 573 m2/g) and 3M $HNO_3$/$LiBH_4$ treatment yielded a sample with an indeterminate surface area (see Table 3).

TABLE 3

Surface area of untreated and treated activated carbon (A.C.)

| A.C. Group | Area (m²/g) |
|---|---|
| Untreated | 1762 |
| 3M HNO$_3$ | 573 |
| 3M HNO$_3$/LiBH$_4$ | N/A |

As shown in FIG. 11, stimulation with all activated carbon samples is well below that of 3M HNO$_3$/LiBH$_4$-treated SWNT bundles. However, the data in FIG. 11 do not account for surface area differences. Thus, antibody presentation was normalized by surface area in 9. This figure additionally shows stimulation by 200 nm polystyrene beads (29 m$_2$/g), C60 and hydroxylated C60 (C60-OH; both estimated (Vogel, et al., *Appl. Phys. A—Mater. Sci. Proc.*, 62:295-301 (1996)) at 4 m²/g). Despite the high surface area of all materials, SWNT bundles on an antibody per area basis displayed the highest activation potential, as demonstrated by the Log [EC50] values (see Table 3), and in agreement with the protein adsorption superiority of this material. These data support the unique capability of SWNT bundles to enhance T cell stimulation.

Example 5. Use of SWNTs as Vaccine Adjuvants

Adjuvants are critical components of vaccines. When mixed with an antigen, they enhance the antigen-specific immune response after immunization. Currently, there are a limited number of adjuvants approved for clinical use (aluminum based salts and a squalene-oil-water emulsion MF59). Adjuvants can activate antigen-presenting cells (APCs) to stimulate T cells more efficiently, natural killer cells (NK cells), or other cells of the innate system to produce cytokines or promote survival of antigen-specific T cells.

In this study, single walled carbon nanotubes (SWNT) were assessed for possible adjuvant properties using the model antigen ovalbumin (OVA). Recent studies have elucidated the potential of SWNT to activate complement via both classical and alternative pathways, as well as their capacity to provoke inflammation and granuloma formation (Salvador-Morales, et al., *Molecular Immunology*, 43:193-201 (2006)).

C57BL6 mice were treated subcutaneously with either OVA alone, with OVA adsorbed to alum, with OVA adsorbed onto SWNT bundles, or with phosphate-buffered saline as a vehicle control. Details of the experimental conditions are provided in Table 4.

TABLE 4

Experimental conditions for vaccination

| Treatment Group | Dose |
|---|---|
| SWNT + OVA | 100 µg in 0.3 ml of PBS adsorbed to 25 µg/ml SWNT per mouse |
| Alum + OVA | 1 µl of Alum per 1 µg of OVA, 0.3 ml Tris buffer |
| OVA alone | 100 µg OVA in 0.3 ml of PBS per mouse |
| PBS | 0.3 ml PBS per mouse |

Three mice were used for each condition. Serum was collected from all animals prior to dosing. Mice were injected subcutaneously and were euthanized 10 days later for collection of serum and spleens.

Figure 13:
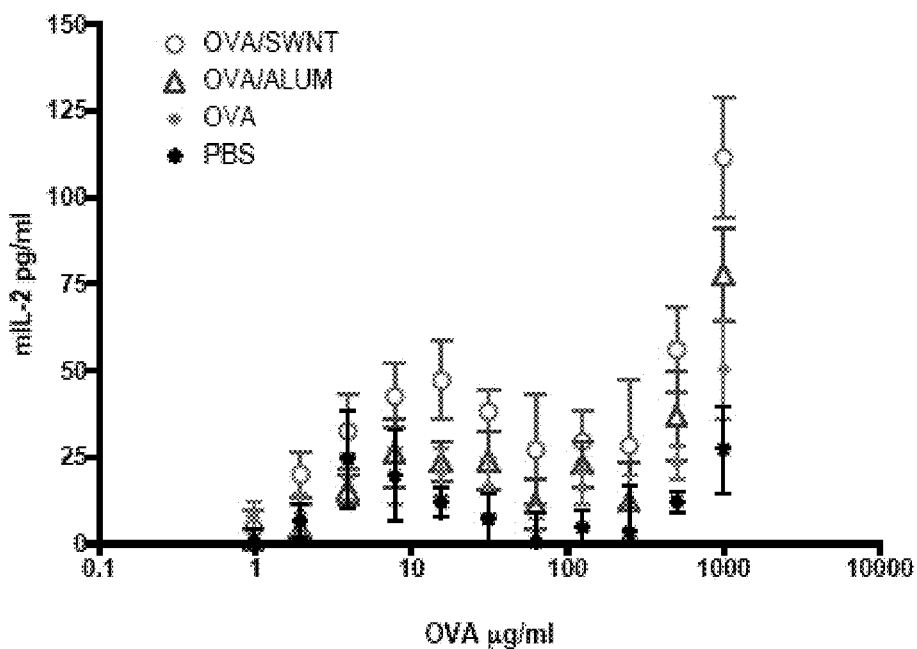
FIG. 13 is a line graph showing activation of spleenocytes obtained from mice vaccinated subcutaneously with ovalbumin (OVA) alone (-◆-), OVA adsorbed onto SWNTs (-○-), OVA adsorbed onto alum (-Δ-), or phosphate buffered saline (PBS) (-*-), as a control. Spleenocytes obtained from the mice were activated with OVA at the indicated concentration. Spleenocyte activation was determined by measuring secretion of IL-2 and data are expressed as the amount of IL-2 secreted (pg/ml) as a function of the concentration of added OVA (µg/ml).

OVA specific antibody T cell responses were analyzed by isolation of spleenocytes from animals post euthanization. Spleenocytes were challenged with OVA to assess cellular immune induction. Induction was determined by measuring the production of Il-2 by the spleenocytes. Cellular immunity was positive for the SWNT OVA group across a range of titrated antigen (FIG. 13). Responses of spleenocytes from mice from all other treatment groups was lower, including from the mice treated with Alum, which is a gold standard adjuvant.

Figure 14:
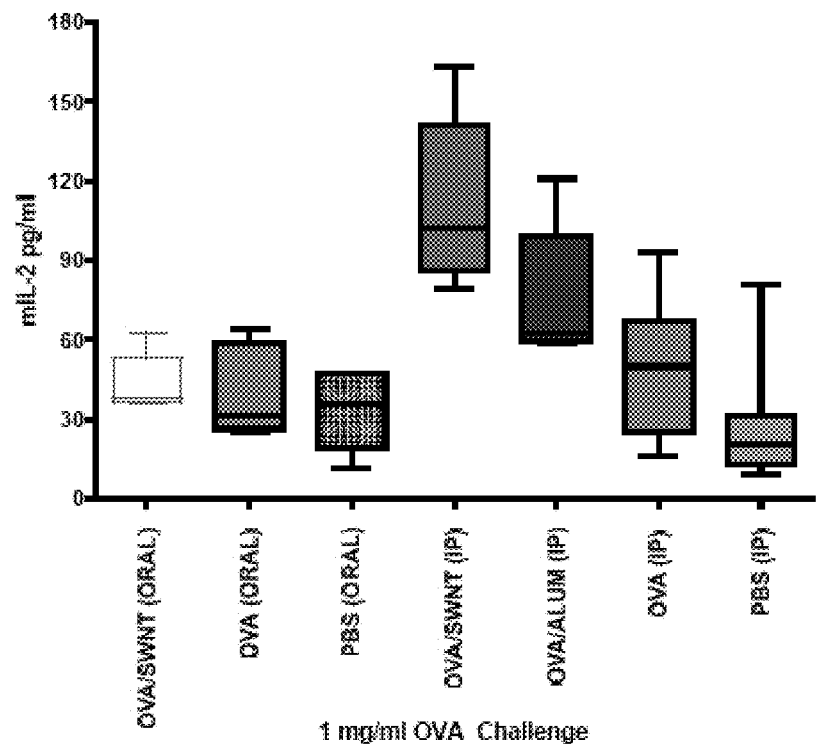
FIG. 14 is a graph showing activation of spleenocytes obtained from mice vaccinated intraperitoneally or orally with OVA, OVA adsorbed onto SWNTs, OVA adsorbed onto alum, or PBS, as a control. Spleenocytes obtained from the mice were activated with OVA at 1 mg/ml. Spleenocyte activation was determined by measuring secretion of IL-2 and data are expressed as the amount of secreted IL-2 (pg/ml).

Similarly, when mice were immunized intraperitoneally and orally with OVA adsorbed to SWNT bundles, T cells obtained from the immunized mice demonstrated strong induction of IL-2 in response to challenged with OVA at 1 mg/ml (FIG. 14).

Example 6. Design and Characterization of CNPs for Clustered Antigen Presentation, IL-2 Delivery, and Magnetic Enrichment of Activated T Cells Materials and Methods Carbon Nanotubes Bundled CNTs were synthesized from cobalt-incorporated MCM-41, purified using a four-step treatment procedure, oxidized in 3M nitric acid (Sigma Aldrich, St. Louis, Mo.), then reduced in lithium borohydride (Sigma Aldrich) as published previously. See Chen et al. (2007), *ACS Nano* 1:327-336 and Fadel et al. (2008), *Nano Letters* 8:2070-2076. CNT suspension (50 µg/mL) in Phosphate Buffer Saline (PBS) (Thermo Scientific, Waltham, Mass.) was sonicated for 10 min to obtain uniform dispersion, and then re-suspended in a 0.8 M solution of neutravidin (Invitrogen, Carlsbad, Calif.) in PBS to obtain $^N$CNTs. The mixture was allowed to mix in a rotary shaker at 4° C. overnight.

Synthesis of Magnetite

Iron acetylacetonate (Fe(acac)$_3$) (0.399 g, 1.56 mmol), oleic acid (1.50 mL, 4.64 mmol), oleylamine (1.03 mL, 3.09 mmol), 1,2-hexadecanediol (2.03 g, 7.76 mmol) and benzyl ether (10 mL) (all obtained from Sigma Aldrich) were added to a single-neck round bottom flask equipped with a magnetic stir bar and a condenser, and deoxygenated for 1 hr. The reaction was gradually heated at 3° C./min to 200° C., and held at that temperature for 3 hr before cooling at room temperature. A final black solution was observed. The reaction mixture was precipitated in ethanol (Sigma Aldrich) and centrifuged twice. Ethanol was decanted and the product was dried via nitrogen purge leaving a black powder.

Preparation of IL-2/Magnetite Co-Loaded Nanoparticles with Biotin Surface Functionality (NPs)

50 µL of recombinant proleukin human IL-2 (Novartis, East Hanover, N.J.) at 1.2 mg/mL in PBS was added dropwise to a vortexing solution of Poly(D,L-lactide-co-glycolide) (PLGA) 50:50 (100 mg) with an inherent viscosity of 0.59 dL/g (Lactel Polymers, Inc. Pelham, Ala., USA) and hydrophobic magnetite (18 mg) dissolved in 2 mL chloroform (Thermo Scientific). The mixture was added dropwise to a 3.2 mL of a vortexing solution of 5% polyvinyl alcohol (PVA, Sigma-Aldrich) with MW average 30-70 kD and DSPE-PEG-Biotin (4.14 mg/0.828 mL) (Avanti Polar Lipid, Alabaster, Ala.). The resulting mixture was then sonicated 3 times for 10 s at 38% amplitude (TEKMAR VCW 400 W). The solution was added dropwise to 100 mL of 0.2% PVA, and left stirring for 3 hr to evaporate the solvent. Particles were collected by centrifugation at 12,000 rpm for 15 min at 4° C., then washed 3 times with de-ionized water. NPs were lyophilized and stored at −20° C. until use. NPs with varying amounts of magnetite were also prepared in identical fashion.

Transmission Electron Microscopy (TEM)

TEM examination NPs and gold-tagged neutravidin adsorbed on bundled CNTs were evaluated on a Tecnai T12 HR-TEM (FEI Company, Hillsboro, Oreg.) operating at 120 kV. Neutravidin was previously conjugated with a stoichiometric amount of biotinylated gold nanoparticles with a diameter of 10 nm (NANOCS, New York, N.Y.). Digital electron micrographs were acquired with a high-resolution 4 k×4 k GATAN Ultrascan CCD camera (Pleasanton, Calif.). A drop of well-dispersed particle suspension was placed on an EMS carbon film 400 mesh copper grid (E.M.S., Hatfield, Pa.), then dried at ambient conditions prior to placement in the sample holder of the microscope.

Scanning Electron Microscopy (SEM)

XL-30 ESEM FEG (Philips, Andover, Mass.) was used to visualize bundled CNTs and CNPs. The particles were fixed on an aluminum stub using 2-sided carbon tape (E.M.S). The samples were imaged using a LaB electron gun with an accelerating voltage of 5-10 kV. Size distribution and average particulate diameter of bundled CNTs were determined by analyzing approximately 142 particulates per image using the freeware program NIH ImageJ.

Nanoparticle Size and Separation Analysis

NanoSight (Amesbury, U.K.) with an NS500 Microscope and NTA 2.0 Software was used to visualize and determine the size distribution, concentration, and degree of nanoparticles. NPs were dispersed in PBS at dilute concentrations prior to analysis (125 μg/mL). NanoSight's "Nanoparticle Tracking Analysis" (NTA) detects and visualizes populations of nanoparticles in liquids and measures the size of each particle from direct observations of diffusion as well as concentration in number of particles per milligram of sample. NPs were first purified immediately after synthesis by a 10 min separation using a 0.5 T magnet. Separation of CNPs involved two 10 min periods of separation. The supernatant was poured out and analyzed by NanoSight or flow cytometry.

Inductively Couple Plasma Mass Spectrometer (ICP-MS)

The iron content of NPs were determined by using an inductively couple plasma mass spectrometer (ICP-MS) (ELEMENT XR, Thermo Scientific). 56Fe was measured using medium resolution (4000) and high resolution (10000) mass/mass difference. Under these conditions, 40Ar16O, which only needs a resolution of ~2500 (mass/mass difference), was readily distinguished from 56Fe. Concentrated nitric acid and hydrogen peroxide (Sigma Aldrich) were added to completely digest the samples to release iron for analysis.

Controlled Release of IL-2

17.5 mg of NPs were transferred to 1.7 mL Eppendorf tubes, suspended in 0.350 mL PBS and incubated at 37° C. on a rototorque for a week. Periodic sampling of the amount of IL-2 released from the nanoparticles was performed by centrifuging the nanoparticles, removing 0.350 mL of the supernatant for analysis and the re-suspending the nanoparticles in 0.350 mL of fresh buffer. Enzyme-linked immunosorbent assay (ELISA) analysis was performed to measure IL-2 levels according to the manufacturer's guidelines (BD Biosciences, San Jose, Calif.).

FRET Sample Preparation and Analysis

Donor-only (5 μg/mL), acceptor-only (5 μg/mL), and donor-acceptor samples (2.5 μg/mL each) were prepared by incubating $^N$CNTs (25 μg/ml) with goat anti-mouse IgG-2a tagged with Alexa Fluor 555 (AF555) (Molecular Probes Inc., Eugene, Oreg.) as the donor, goat anti-mouse IgG-2a tagged with Alexa Fluor 647 (AF647) (Molecular Probes Inc.) as the acceptor, or an equimolar mixture of both. In each case, FRET antibodies were bound to stoichiometric amounts of biotinylated anti-goat IgG (R&D Systems, Minneapolis, Minn.) before binding $^N$CNTs. Samples were tumbled at room temperature for 1 hr, away from light. Samples were then washed twice in PBS. A fourth group of CNT without a FRET pair was included as a control. FRET acceptor photobleaching (FRET-AP) was performed using a Leica SP5 microscope (Allendale, N.J.), and images were processed using Leica LAS AF (including FRET efficiency analysis) and MATLAB as previously described in Fadel et al. (2010), Langmuir 26:5645-5654.

Results

Figure 2:
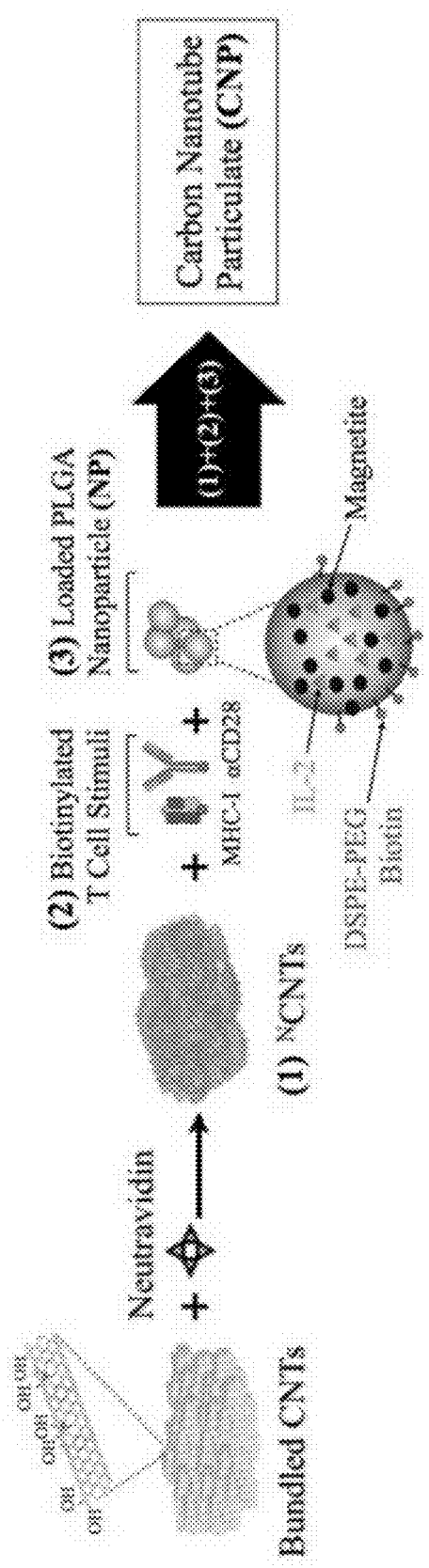
FIG. 2 is a schematic showing the design of carbon nanotube particulates (CNPs) for multivalent antigen presentation, paracrine delivery of cytokine, and T cell enrichment. The first step involves bundling neutravidin functionalized CNTs. Stochiometric amounts of biotinylated T cell antigens are then added to be presented on the CNT surface. PLGA nanoparticles loaded with magnetite and IL-2 are bound to the antigen presenting CNTs surface to yield the CNPs.
Figure 3:
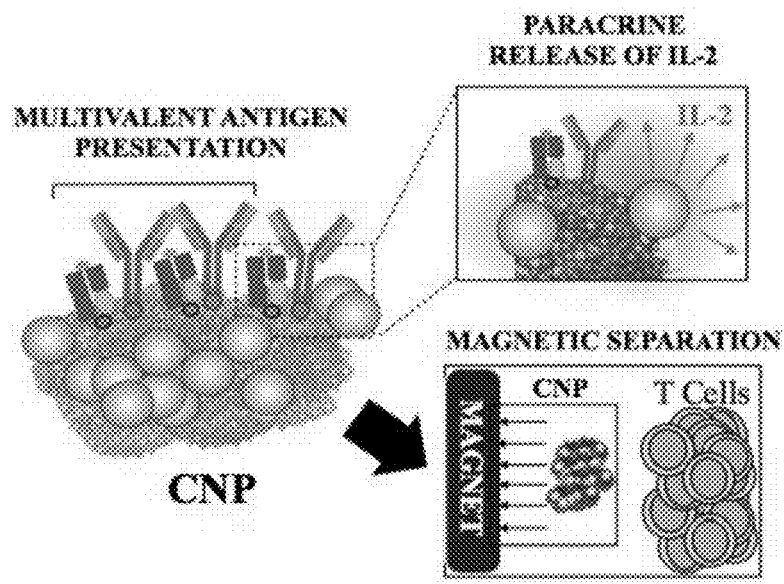
FIG. 3 is a schematic highlighting three properties of the engineered CNP platform: multivalent antigen presentation, paracrine release of IL-2, and magnetic separation/enrichment of CNPs from T cells.
Figure 4:
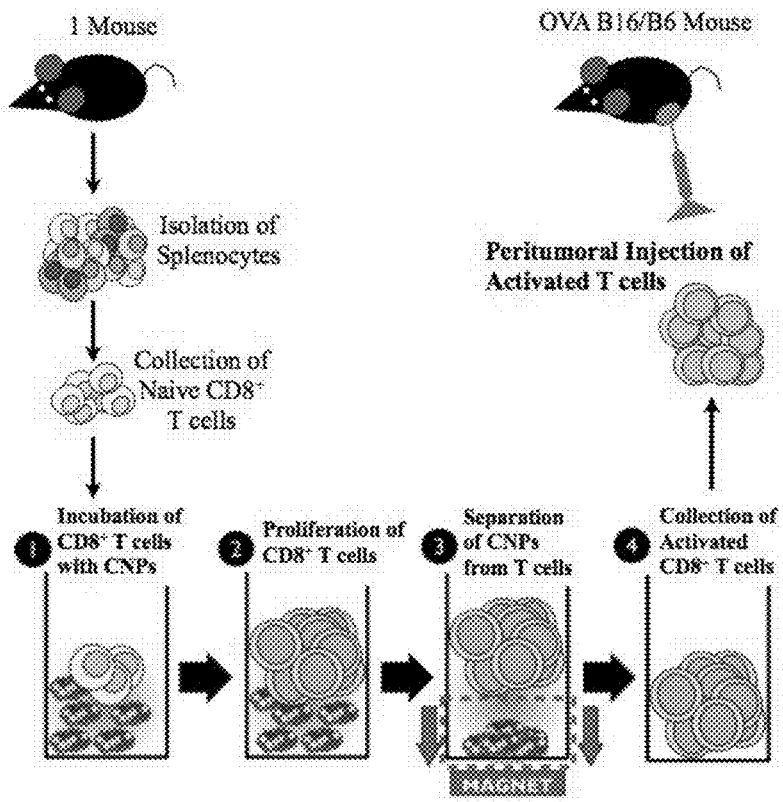
FIG. 4 is a schematic showing the work flow for a T cell stimulation process and cell separation using CNPs; OT-1 CD8+ T cells were purified from splenocytes, and incubated with CNPs for three days; activated T cells were then magnetically separated from CNPs, collected, and injected peritumorally in B6 mice, which were previously inoculated with the B16 tumor for ten days.

CNTs were synthesized as described above, treated with 3M $HNO_3$, then reduced in $LiBH_4$ to yield ultra-pure, hydroxyl-modified CNTs, which were rich in surface defects and presented a high surface area as previously measured. See Fadel et al. (2008), Nano Letters 8:2070-2076; Fadel et al. (2010), Langmuir 26:5645-5654; and Fadel et al. (2012) Small. In the scheme shown in FIG. 2, a protein linker, neutravidin, was adsorbed to yield $^N$CNTs, then stoichiometric amounts of biotinylated T cell stimulatory signals added. This simple method has been previously demonstrated to yield the stable presentation of physiological T cell antigens such as MHC-I. See Fadel et al. (2012) Small. A third crucial signal in the design is local paracrine delivery of cytokines to T cells. By binding NPs co-encapsulating IL-2 and magnetite to $^N$CNTs, multivalent presentation of physiological T cell stimulatory signals was integrated with paracrine delivery of IL-2, and enabled the magnetic separation of CNPs from T cells (FIG. 3). This is tested by first stimulating ovalbumin-specific CD8$^+$ T cells directly isolated from transgenic mice (OT-1), then measuring the therapeutic efficacy of these activated T cells in vivo in mice inoculated with melanoma cells expressing the ovalbumin antigen (B16-OVA) following magnetic separation from CNPs (FIG. 4).

TABLE 5

Physiochemical properties of two main components of CNP.

| Property | Functionalized CNT | NP |
|---|---|---|
| Diameter | ~0.8 nm/nanotube | ~150-200 nm/particle |
| Length | ~0.5-5 μm/tube<br>~20-40 μm/assembly | N/A |
| Zeta Potential (in $H_2O$) | −2.6 mV | −2.2 mV |
| Zeta Potential (in buffer) | −26.4 mV | −5.0 mV |
| Surface Group | 1745 m$^2$/g | 5 · 10$^{-13}$ m$^2$/particle |
| Functional Group | Hydroxyl | PEG-Biotin |
| Magnetite Loading | N/A | 12% by weight of PLGA |
| Protein Loading | ~8 nmol of neutravidin/mg CNT | ~50 μg IL-2/100 mg PLGA |
| Concentration Used in Culture | 5 μg/mL | 125 μg/mL |
| Amount of Antigen Presented | 2.1M | N/A |

Figure 15:
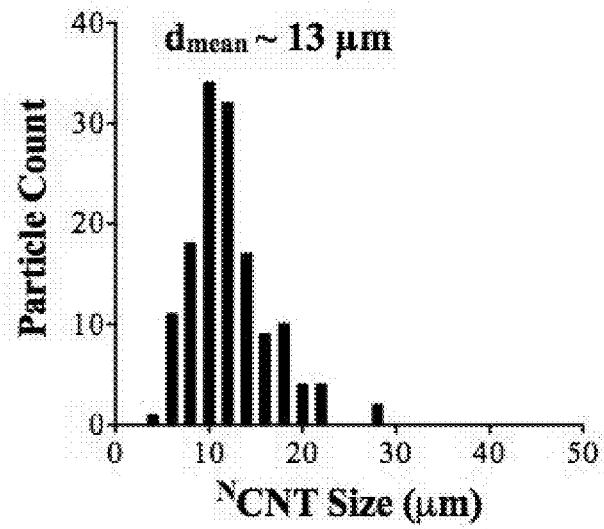
FIG. 15 is a bar graph showing the size distribution of bundled CNT microparticles extracted from SEM images and using NIH ImageJ software (n=142 particles).
Figure 16:
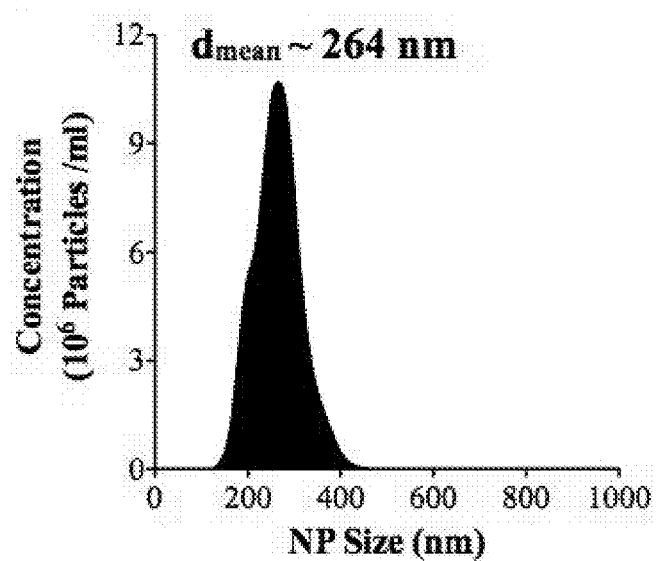
FIG. 16 is plot of the size distribution of the magnetite and CL-2 loaded PLGA nanoparticles using nanoparticle tracking analysis.

Progression of the platform from bundled CNTs into CNPs was observed by SEM and TEM. SEM and TEM images showed the presence of structural gaps in CNTs that are amenable for the adsorption of proteins, and SEM images of the successful integration of $^N$CNTs with NPs. Encapsulation of magnetite in NPs and the qualitative binding of neutravidin-gold to bundled CNTs by TEM was confirmed. The size of the CNT bundles was determined from the SEM images using ImageJ for 142 particles. The size distribution of the CNT bundles is plotted in FIG. 15. CNTs were determined to bundle into particles of ~13 μm in diameter and were functionalized to yield surface defects, thus resulting in a higher surface area. The physiochemical properties of the CNTs and NPs are summarized in Table 5. The size of the magnetic loaded NPs was determined by nanoparticle tracking analysis. The distribution of NP sizes is plotted in FIG. 16. The diameter of NPs was estimated around approximately 264 nm from this distribution. Biotin-PEG functionality on the NP surface was confirmed by $^1$H NMR spectroscopy with the presence of the methylene protons from the PEG segment appearing at approximately 3.5 ppm. As expected, NPs exhibited superparamagnetic properties at room temperature as determined by superconducting quantum interference device (SQUID) analysis. The adsorption isotherm of neutravidin on CNTs also showed saturation at 8 nmol of protein/mg CNT. Additional studies determined that optimal T cell stimulation was achieved using 5 μg/ml of CNT, 125 μg/ml of NP, and a 2.1 μM concentration of biotinylated MHC-I and μCD28. Comparing $CD8^+$ T cell response using avidin or streptavidin-bound CNTs ($^A$CNTs and $^S$CNTs, respectively) to $^N$CNTs in similar experimental conditions indicated that, although the amount and distribution of protein is the same in all three platforms, the charge microenvironment provided by $^N$CNTs was more optimal for the stimulation of T cells.

TABLE 6

Effect of magnetite loading on magnetic separation, IL-2 release and T cell stimulation

| | Percent Loading of Magnetite in NP | | |
|---|---|---|---|
| | 6 wt % | 12 wt % | 30 wt % |
| % Separation Efficiency | 72.5 ± 4.9 | 97.7 ± 1.0 | 95.8 ± 1.2 |
| Il-2 Released (pg/10$^{10}$ particles) | 773.5 ± 47.4 | 480.5 ± 9.2 | 293.9 ± 1.6 |
| T cell response (pg IFN-γ/mL) | 1622.5 ± 834.4 | 5056.3 ± 595.7 | 3122.5 ± 413.7 |

Figure 17:
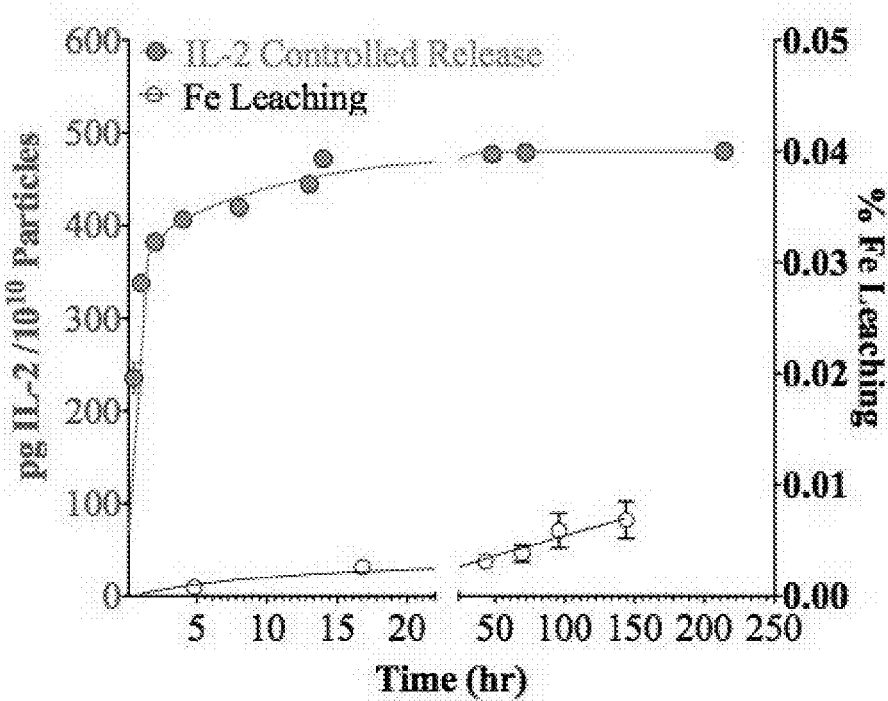
FIG. 17 is graph showing the encapsulated IL-2 (solid grey circles, left axis) and iron (empty circles, right axis) release from magnetite and CL-2 loaded PLGA nanoparticles over a 1-week period. The results are mean values from three independent experiments with error bars representing ±SEM.

To investigate the impact of magnetite loading on IL-2 release from NPs and subsequent T cell stimulation, loading of magnetite by weight percent (wt %) was varied between 6 wt %, 12 wt % and 30 wt %. The results are summarized in Table 6. First, the results indicate that there is a strong correlation between the wt % of magnetite and the number of NPs encapsulating magnetite. For example, doubling magnetite loading from 6 wt % to 12 wt % results in half as many particles, close to 0.8×10$^{10}$ particles. Second, varying the wt % of magnetite co-encapsulated with a same amount of IL-2 in NPs significantly affected a seven-day cumulative release of cytokine on a-per-particle basis. Third, CD8$^+$ T cells incubated with CNPs at various wt % loading of magnetite showed an optimal IFN-gamma response at day 3 to particles loaded at 12 wt % using equal particle concentration in all three groups. Finally, overall separation efficiency of T cells from CNPs was measured to be above 95% at a magnetite loading of 12 and 30 wt %. Thus, by designing CNPs containing NPs loaded with 12 wt % magnetite, cell separation efficiency was measured at approximately 98% using flow cytometry. The NP scatter profile located at low forward scatter (FSC) indeed decreased from 8.59% of gated population to 0.17% after magnetic separation. Images of samples before and after separation indicated successful separation of CNPs from cells. To visualize protein cluster formation on the surface of CNT bundles, secondary antibody pairs, either with acceptor or donor fluorescence probes each bound to a biotinylated primary antibody, were allowed to bind to $^N$CNTs. Fluorescence images of both donor and acceptor channels were observed after addition to $^N$CNTs. Acceptor photobleaching of the antigen-bound $^N$CNT platform triggered an increase in donor emission. The representative FRET efficiency map derived from the change in donor emission clearly pointed to the presence of several micron-scale antigen clusters. The FRET efficiencies were measured to be 60-70%. Finally, the presentation of biotin on NPs was achieved using fatty acids and lipids as hydrophobic anchors to strongly associate with the PLGA matrix. This biotinylation further affords the attachment to the $^N$CNT platform and allows co-encapsulation and prolonged retention of fatty acid-modified magnetite. We measured the cumulative release of IL-2 and iron from NPs loaded with 12 wt % magnetite. The release profile of IL-2 and iron from the 12 wt % magnetite NPs is plotted in FIG. 17. The controlled release profile of IL-2, measured over a period of more than a week, is typical of protein release during PLGA degradation. See for example Steenblock and Fahmy (2008), *Mol. Ther.* 16:765-772 and Steenblock et al. (2011), *J. Biological Chem.* 286:34883-34892. It is characterized by an initial burst release followed by continual release of protein over time. Leaching of iron from NPs was negligible over 150 hours, and was measured below 0.01% of total iron loaded in the particles.

Example 7. In Vitro Stimulations of CD8+ T Cell Effectors by CNPs Material and Methods Antigen-Specific T Cell Stimulation Studies.

OT-1 mice (in which CD8+ T cells express a transgenic TCR specific for the SIIN peptide of ovalbumin presented on H-2K$^b$) were bred, maintained, and screened in the Malone Engineering Center at Yale University. Splenocytes were isolated from the spleen of OT-1 mice (aged 6-8 weeks) after depletion of erythrocytes by hypotonic lysis. CD8$^+$ T cells were isolated using a CD8$^+$ negative selection kit (StemCell Inc., Vancouver, Canada). CD8$^+$ T cells were resuspended in cell media, composed of RPMI 1640 supplemented with FBS (10%), L-glutamine (1%), HEPES buffer (1%), non-essential amino acids, 2-ME (0.1%), penicillin (2%), and stored at 4° C. before use. Equimolar amount (2.1 nM total) of biotinylated H-2K$^b$ loaded with SIINFEKL peptides (MHC-I) and anti-CD28 (BD Biosciences) were added to the $^N$CNT suspension, and allowed to mix for 1 hr at room temperature. As a final step, NPs (625 μg/mL) were added to the mixture and allowed to bind for ½ hour. The mixture was then diluted in cell media (1:5) then added to an equal volume of CD8$^+$ T cells (5×10$^5$ cells/mL) in a 24-well plate. For control groups, DYNABEADS® (Invitrogen) were added at a final concentration of 1×10$^6$ particles/mL, in similar cell culture conditions to CNPs. The cells were then incubated at 37° C. After three days of culture, samples were collected by group (including supernatant for cytokine analysis), purified using magnetic separation to isolate activated T cells, counted, and sized using a Multisizer 3 Coulter counter at a 1:400 dilution (Beckman Coulter Inc., Indianapolis, Ind.), then processed for analysis. For long-term expansion studies, T cells collected at day 3 were re-stimulated using a same quantity of soluble MHC-I and αCD28, along with exogenous IL-2 or NPs depending on the groups. Cells were activated using CNPs for the first 3 days to avoid effects related to T cell exhaustion and activation-induced cell death. At day 5, 7, and 14, T cells will be collected, purified using magnetic separation, counted and sized, and re-stimulated using similar conditions to day 3.

Immunofluorescence

After separation, CD8+ T cells were washed twice in a staining buffer solution (1% BSA in PBS), and adjusted at a concentration of 5×10⁶ cells/mL. For cell surface staining, T cells were resuspended in staining solutions containing antibody mixtures at a ratio of 1:400 in staining buffer for 30 min at 4° C. A six-color combination was selected using the following antibodies: anti-CD44 FITC, anti-CD8 PacBlue, anti-CD25 AF700, anti-CD62L APC, anti-CD27 PE, anti-CD69 PE-Cy7 (eBiosciences). After incubation, cells were washed twice in staining buffer then resuspended in 4% paraformaldehyde (PFA) (USB Corp., Cleveland, Ohio) before measurement. For intracellular staining, CD8+ T cells were incubated in the presence of GolgiPlug™ (BD Biosciences) for 4 hr, washed twice in Perm/Wash™ solution (BD Biosciences), and resuspended in 250 µl of Cytofix/Cytoperm™ (BD Biosciences) solution for 20 min at 4° C. T cells were washed twice in Perm/Wash™ solution then resuspended in a staining solution containing anti-granzyme-B PE-Cy7 (eBiosciences) at a ratio of 1:400 in staining buffer for 30 min at 4° C. After incubation, cells were washed twice in PERM/WASH™ then resuspended in 4% PFA before measurement. Flow cytometry measurements were performed using a Becton Dickinson LSR-II (San Jose, Calif.) with appropriate compensation and staining controls. Analysis of fluorescence was performed using FlowJo software (Tree Star, Ashland, Oreg.) and gating on CD8+ subsets in side scatter (SSC) vs. forward scatter (FSC) plots. Granzyme-B mean fluorescence was normalized to the mean fluorescence measured in CNP-activated T cells.

Imaging of CD8+ T Cells

Expansion of CD8+ T cells was imaged using an inverted phase-contrast Eclispse TS100 microscope (Nikon Inc., Melville, N.Y.) in a 24-well plate at 24, 48, and 72 hr of culture. 20× and 100× images were captured using a high-resolution digital camera DXM1200F (Nikon, Melville, N.Y.). Interaction of T cells with CNPs was imaged using a Leica SP5 confocal microscope and analyzed using Leica LAS AF. T cells were cultured in presence of CNPs (or appropriate controls) in 4-well Lab-Tek™ chamber slide system (Thermo Scientific) as described above. After 24 hr of culture, the slide system was centrifuged at 1500 rpm, washed twice in staining buffer. Cell surface staining was performed using CD25-FITC (eBiosciences) at 1:400 in staining buffer for 1 hr at room temperature away from light. The slide system was then washed twice in staining buffer then immersed in 0.1% Triton-X (Sigma-Aldrich). Intracellular staining was performed using anti-granzyme-B AF647 (eBiosciences) at 1:400 in staining buffer for 1 hr at room temperature away from light. Following another two washes in staining buffer, actin staining was performed using Phalloidin-Texas Red X (Invitrogen) at a ratio of 1:200 in PBS and incubated for 1 hr at room temperature away from light. Finally, the samples were washed in PBS twice, and a drop of Vectashield with DAPI (USB Corp.) was added to a microscope slide before mounting the coverslip.

Cell-Mediated Cytotoxicity

Lactate dehydrogenase (LDH) release assay (Roche, Penzberg, Germany) was used to measure CD8+ T cell lytic activity against B16F10-OVA target cells in vitro according to the manufacturer's guidelines. Briefly, B16F10-OVA cells were cultured in DMEM media with 10% FBS and 2% penicillin. After confluence, cells were dissociated using trypsin EDTA (Invitrogen). A total of 1·10⁴ target cells were incubated with serially diluted, previously activated effector T cells in 200 µl assay medium (cell culture media with 2% FBS) in a 96-well plate. After 4 hr, the plate was centrifuged at 1500 rpm, the supernatant was removed, and 100 µl of LDH reaction mixture was added to cells. The plate was incubated at room temperature away from light for 10 min, and absorbance was measured at 492 nm. Percent cell-mediated cytotoxicity was calculated as follows:

100×(experimental−effector spontaneous−target spontaneous)/(target maximum−target spontaneous).

Results

Figure 18:
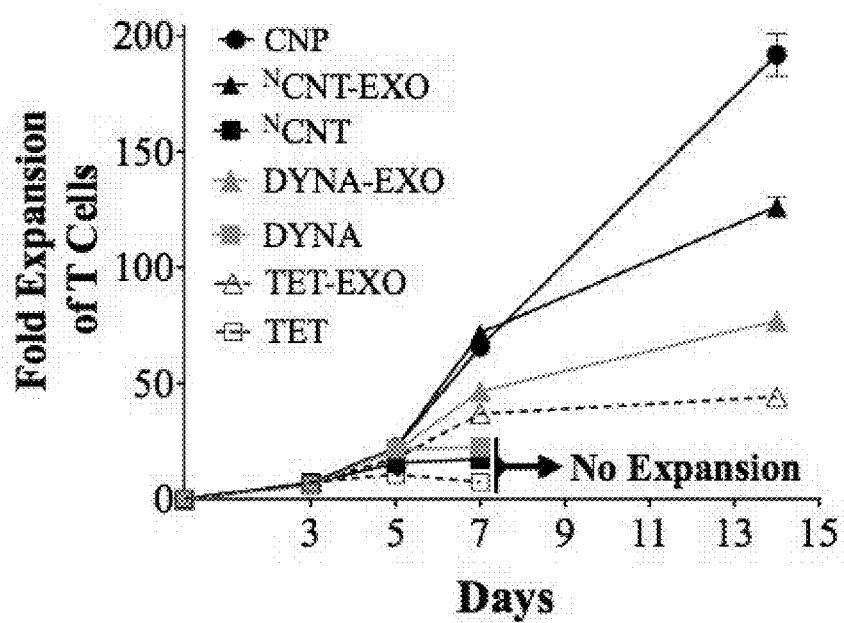
FIG. 18 is a graph showing OT-1 CD8+ T cell expansion measured using coulter-counter during a two-week period. The results are mean values from three independent experiments with error bars representing ±SD.
Figure 19:
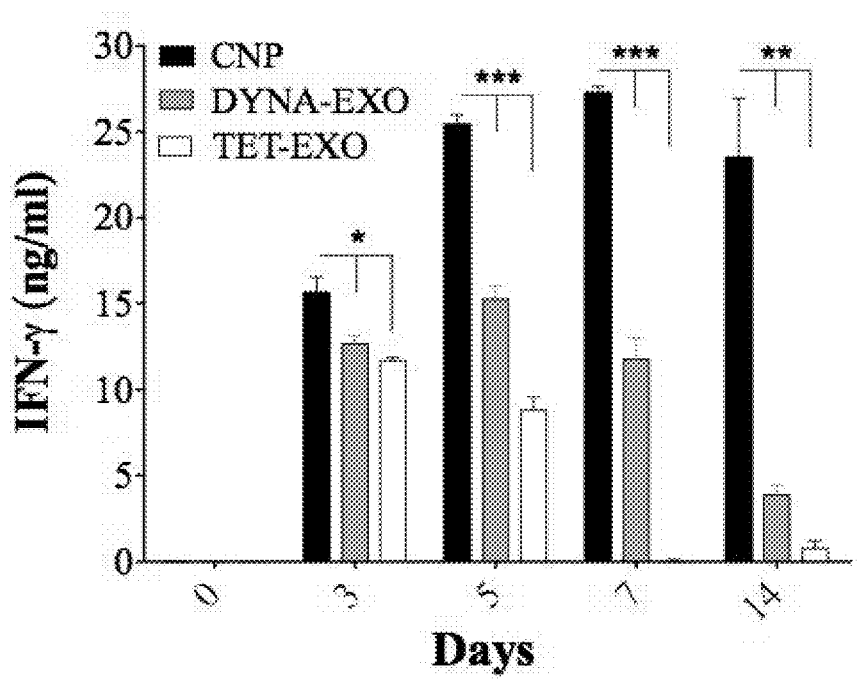
FIG. 19 is a bar graph showing IFN-γ release from OT-1 CD8+ T cells measured at each time point during a two-week period cell expansion. The results are mean values from three independent experiments with error bars representing ±SEM. (*) represents a p-value<0.05, () represents a p-value<0.01, and (*) represents a p-value<0.0001.

The efficacy of CNPs as an aAPC was examined by incubating the CNPs from Example 6 with CD8+ T cells isolated from an OT-1 mouse. FIG. 18 compares expansion as a function of time for T cells interacting with CNPs; $^N$CNTs, Dynabeads® (commercially available magnetic beads), or soluble tetramers presenting antigens with exogenous IL-2 ($^N$CNT-EXO, DYNA-EXO and TET-EXO respectively); $^N$CNTs, Dynabeads®, or soluble tetramers presenting antigens without the addition of IL-2 ($^N$CNT, DYNA and TET respectively). After two weeks, CD8+ T cells expanded about two hundred-fold, more than twice the cumulative expansion of cells interacting with DYNA-EXO, and more than four times the results obtained from TET-EXO. Sizing of cells interacting with these same platforms indicates that these effects on expansion potentially extend to cell phenotype (Table 7). Finally, measurement of IFN-gamma released from these CD8+ T cells parallels previous results on cell proliferation and size (FIG. 19).

Confocal imaging indicated that early interaction of CD8+ T cells with CNPs is characterized by the formation of non-specific cell blasts around the particles and with MHC-I loaded with a null agonist peptide (SIYRYYGL) that does not trigger the OT-1 T cell receptor. Upregulation of effector markers was however observed in T cells interacting with CNPs presenting OT-1-specific antigens. It was characterized with confocal imaging by the presence of cytotoxic granules and by the secretion of granzyme-B. Expression of CD25, the α-chain of the IL-2 receptor, was also observed at the T cell-CNP interphase. As expected, T cells cultured in the presence of CNPs presenting MHC-I loaded with SIYRYYGL peptide did not express CD25 or granzyme-B. T cells incubated with soluble tetramers expressed these effector markers, although not to the same level of fluorescence intensity as what was observed with CNPs. T cell cultures with CNPs displaying agonist peptide were observed with an inverted-phase contrast microscope at 24, 48, and 72 hours. The cultures showed the formation of large lymphoblasts around the particle at 24 hours, and increasing in size through 48 and 72 hours characteristic of vigorous T cell proliferation.

TABLE 7

Effect of CNP on T cell proliferation and cell size as a function of time

| Groups | Days | Fold Expansion | Cell Diameter (µm) |
| --- | --- | --- | --- |
| CNP | 3 | 7.0 ± 0.1 | 9.3 ± 0.1 |
|  | 5 | 22.4 ± 0.9 | 9.2 ± 0.1 |
|  | 7 | 65.8 ± 5.2 | 8.1 ± 0.1 |
|  | 14 | 191.9 ± 15.9 | 7.6 ± 0.0 |
| TET-EXO | 3 | 7.1 ± 0.2 | 8.6 ± 0.0 |
|  | 5 | 17.7 ± 0.5 | 7.6 ± 0.0 |
|  | 7 | 37.0 ± 1.3 | 6.5 ± 0.2 |
|  | 14 | 44.1 ± 3.6 | 6.7 ± 0.0 |

TABLE 7-continued

Effect of CNP on T cell proliferation and
cell size as a function of time

| Groups | Days | Fold Expansion | Cell Diameter (μm) |
| --- | --- | --- | --- |
| DYNA-EXO | 3 | 7.3 ± 0.2 | 8.8 ± 0.1 |
| | 5 | 20.8 ± 0.6 | 7.9 ± 0.0 |
| | 7 | 46.7 ± 1.9 | 6.8 ± 0.1 |
| | 14 | 77.1 ± 3.6 | 7.1 ± 0.1 |

Figure 20:
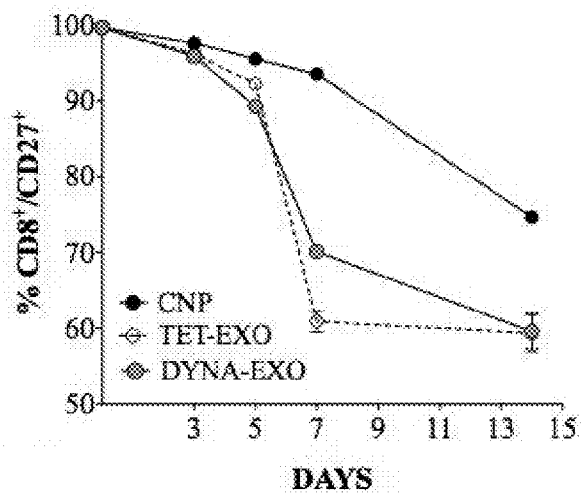
FIG. 20 is a graph showing the effect of CNPs on CD8+ T cell phenotype and cytolytic activity summarizing the percentage of CD8+/CD27+ T cells by group as a function of time. Gating was performed on live T cells.
Figure 21:
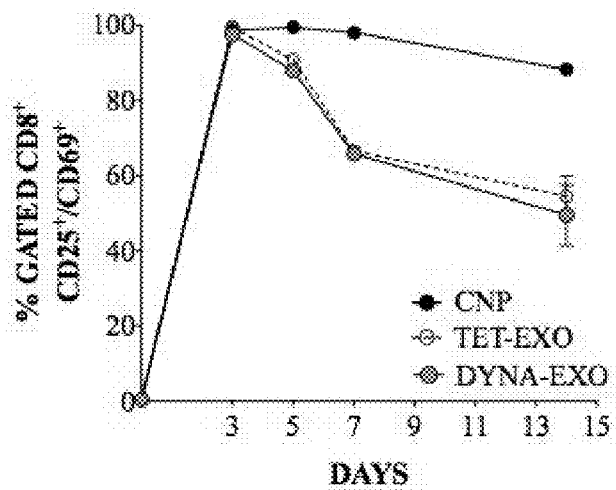
FIG. 21 is a graph showing the effect of CNPs on CD8+ T cell phenotype and cytolytic activity summarizing the percentage of CD25+/CD69+ T cells by group as a function of time. Gating was performed on live T cells.
Figure 22:
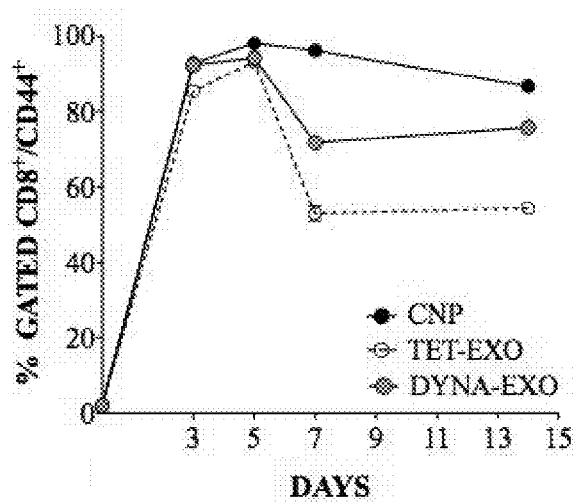
FIG. 22 is a graph showing the effect of CNPs on CD8+ T cell phenotype and cytolytic activity summarizing the percentage of CD44+/CD8+ T cells by group as a function of time. Gating was performed on live T cells.
Figure 23:
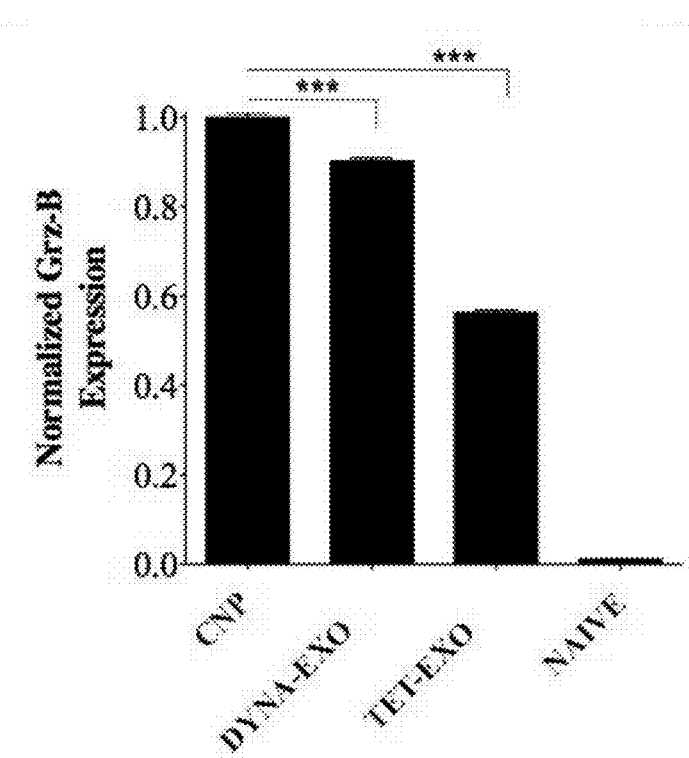
FIG. 23 is a bar graph showing the expression of intracellular granzyme-B at day 3 in OT-1 CD8+ T cells activated by CNPs vs. established controls. (***) represents a p-value<0.0001.
Figure 24:
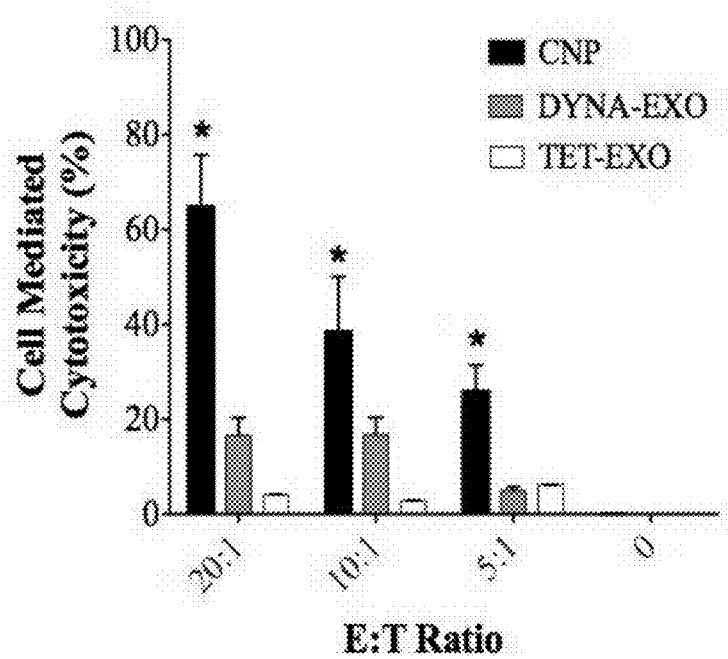
FIG. 24 is a bar graph showing cytotoxic activity of OT-1 CD8+ T cells towards B16 cells presenting MHC-I in the context of OVA. Error bars represent the means ±SEM. All data are representative of at least three independent experiments. (*) represents a p-value<0.05

Flow cytometry analysis of activated cell phenotype indicated that a higher percentage of CD8+ T cells expanded using CNPs retained expression of CD27—a marker of T cell expansion, CD69—an early activation marker, the IL-2 receptor, CD25, and CD62L—an L-selectin adhesion receptor on naïve and central memory T cells. FIG. 20 is a plot of the percentage of CD8+/CD27+ T cells by group as a function of time. The percentage of CD8+/CD27+ T cells activated by CNPs was consistently above 90% during the first week of culture, and was significantly higher than the percentage of CD8+/CD27+ T cells generated by DYNA-EXO and TET-EXO at day 5, 7 and 14. In addition, at least 90% of CD8+ T cells activated by CNPs were CD69+/CD25+ in our culture conditions (see FIG. 21); this portion of cell population was at a significantly larger percentage than what was generated by other platforms at day 5 and thereafter. Furthermore, the percentage of CD8+ T cells expressing a CD44+/CD62L+ phenotype was the highest in the CNP group (See FIG. 22)). Overall, T cells activated by CNPs were able to retain their proliferative capacity and effector phenotype better than control platforms. In addition, expression of granzyme-B in T cells activated by CNPs was significantly higher than lymphocytes cultured with DYNA-EXO and TET-EXO. This is demonstrated in FIG. 23 showing the expression of intracellular granzyme-B at day 3 in OT-1 CD8− T cells activated by CNP as compared to controls. FIG. 24 shows the overall cellular toxicity of OT-1 CD8+ T cells towards B16 cells presenting MHC-I in the context of OVA. Cell-specific cytolytic activity of lymphocytes previously expanded with CNPs and cultured with a melanoma tumor cell line (B16-OVA) was significantly higher compared to other platforms. At E:T ratio of 20:1, specific lysis of target tumor cells was measured ~60% for T cells expanded by CNPs; as much as three times the cytolytic activity observed in cells expanded using conventional, commercially available magnetic beads supplemented with IL-2 in culture (DYNA-EXO).

In Vitro Stimulation with CNPs Requires a Thousand-Fold Less IL-2

Figure 25:
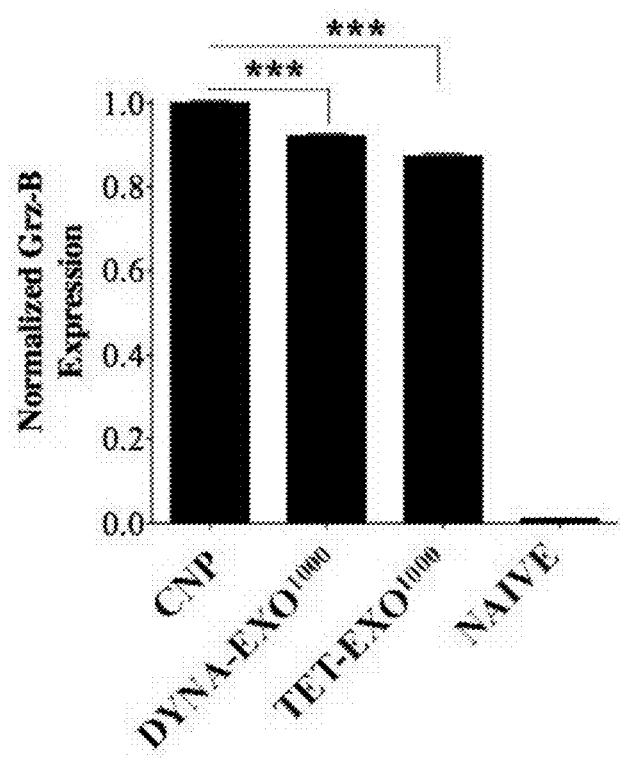
FIG. 25 is a bar graph showing the expression of intracellular granzyme-B at day 3 in OT-1 CD8+ T cells activated by CNPs vs. established controls containing a thousand fold higher exogenous IL-2 concentrations.
Figure 26:
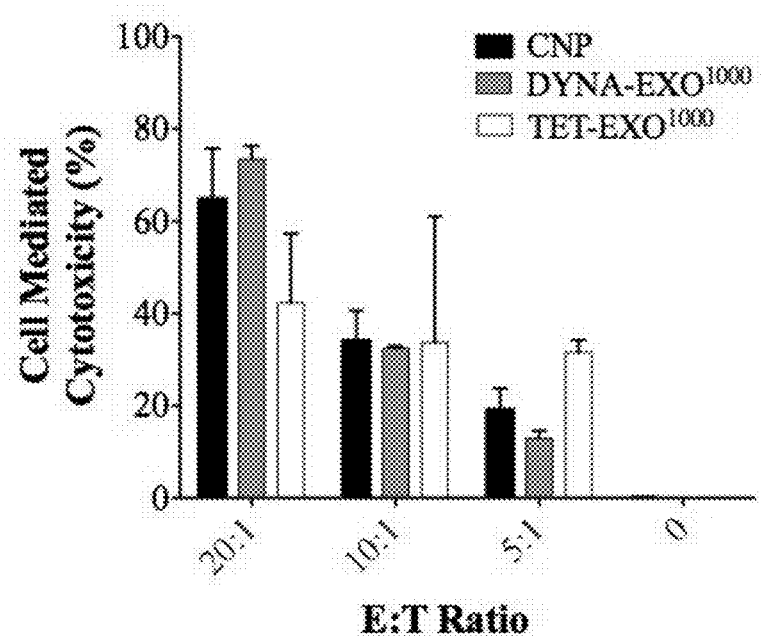
FIG. 26 is a bar graph showing cytotoxic activity of OT-1 CD8+ T cells towards B16 cells presenting MHC-I in the context of OVA vs. controls containing a thousand fold higher exogenous IL-2 concentrations. Error bars represent the means ±SEM. All data are representative of at least three independent experiments.

Previous work has established the importance of IL-2 in increasing the proliferative capacity of T cells. Importantly, a recent study has demonstrated that at least a thousand-fold higher exogenous IL-2 concentrations is required to match the effects of sustained paracrine delivery. See Steenblock et al. (2011), *J. Biological Chem.* 286:34883-34892 and Labowsky and Fahmy (2012), *Chem. Eng. Sci.* 74:114-123. For this reason, we chose to approximate the observed effects of CNPs on CD8+ T cells by adding a thousand-fold more exogenous IL-2 in control groups, and test the therapeutic efficacy of activated T cells in the context of a murine B16 melanoma model. Flow cytometry analysis of the expression of CD69, CD25, CD44 and CD62L expressions from CD8+ T cells cultured for 3 days with either CNPs, Dynabeads® with a thousand-fold more IL-2 (DYNA-EXO$^{1000}$), and soluble tetramers with a thousand-fold more IL-2 (TET-EXO$^{100}$) revealed no significant differences in the percentage of activated T cell populations across the three groups. Control groups significantly upregulated the expression of T cell activation markers, especially CD25 and CD69 when compared to previous day 3 measurements using a thousand-fold less IL-2. FIG. 25 shows the expression of intracellular granzyme-B at day 3 in OT-1 CD8+ T cells activated by CNP vs. DYNA-EXO$^{1000}$ and TET-EXO$^{1000}$. In the context of T cell function, intracellular granzyme-B levels increased for T cells previously cultured with DYNA-EXO$^{1000}$ and TET-EXO$^{1000}$ (by as much as 55% for the latter) as compared to an absence of a thousand-fold excess IL-2. This was found to be consistent with previous studies showing that IL-2 increases the cytolytic function in a dose-dependent manner during the primary activation of murine CD8+ T cells in vitro. FIG. 26 depicts the cellular cytotoxicity of OT-1 CD8− T cells towards B16 cells presenting MHC-I in the context of OVA, comparing T cells activated by CNP vs. DYNA-EXO$^{1000}$ and TET-EXO$^{1000}$. The observed increase in intracellular granzyme-B for T cells cultured using control groups resulted in a significant enhancement in cell-specific cytolytic activity. For instance, specific lysis of target tumor cells at an E:T ratio of 20:1 was found to be similar in CD8+ T cells previously cultured with CNPs, DYNA-EXO$^{1000}$, and TET-EXO$^{1000}$.

Example 8. Adoptive Immunotherapy with CNP Expanded T Cells in Murine Melanoma Model Materials and Methods In Vivo B16 Melanoma Study C57BL/6 Mice were accommodated in autoclaved microisolator cages that were housed in a positive pressure containment rack, and maintained under the guidelines of an approved protocol from the Yale University Institutional Animal Care and Use Committee. Mice were randomly assigned to groups of six animals each. The xenografts of melanoma were developed by subcutaneously implanting $5\times10^6$ B16F10-OVA in the right flank of the mice. After 10 days of tumor inoculation, each mouse was treated with activated OT-1 CD8+ T cells by direct injection into the tumor. The tumor inhibition activity was determined with the tumor volume, which was calculated by the following equation: $V=(w)^2\times(l)/2$, where (w) and (l) were the width and length of the tumor as measured by a caliper. Animals were sacrificed when they met any of the following conditions: (1) 15% loss in initial body weights (2) the size of the tumor 1.5 cm in any dimension, (3) the mouse became lethargic, sick or unable to feed, (4) the mouse developed an ulcerated tumor.

Isolation of Tumor Infiltrating Lymphocytes (TIL)

Subcutaneous B16 melanoma tumors were resected from mice, weighed, minced, and then placed in a serum-free RPMI media containing 175 U/mL of Collagenase IA (Sigma-Aldrich). The resulting tissue suspension was incubated at 37° C. for 1 hr, passed through a 70-μm tissue filter, and the resulting cells were washed twice in serum free RPMI media. The pellet was re-suspended in 0.5 mL of RPMI media then overlaid over mouse lympholyte-M media (Accurate Chemical, Westbury, N.Y.) for lymphocyte isolation, followed by centrifugation at 1500 rpm per the manufacturer's instructions. The resulting buffy coat layer was removed and washed in RPMI media and subsequently re-suspended in 1 mL of staining buffer. All cell suspensions were counted to determine absolute numbers of isolated TILs and subsequently distributed to FACS tube for FACS staining and analysis.

Immunohistochemistry

Resected tumor tissue was fixed in 10% formalin for 24 hrs. and embedded in paraffin. Preparation of slides, sectioning, and haematoxylin-and-eosin (H&E) staining were performed by the Yale histology and pathology laboratory.

Results

Figure 27:
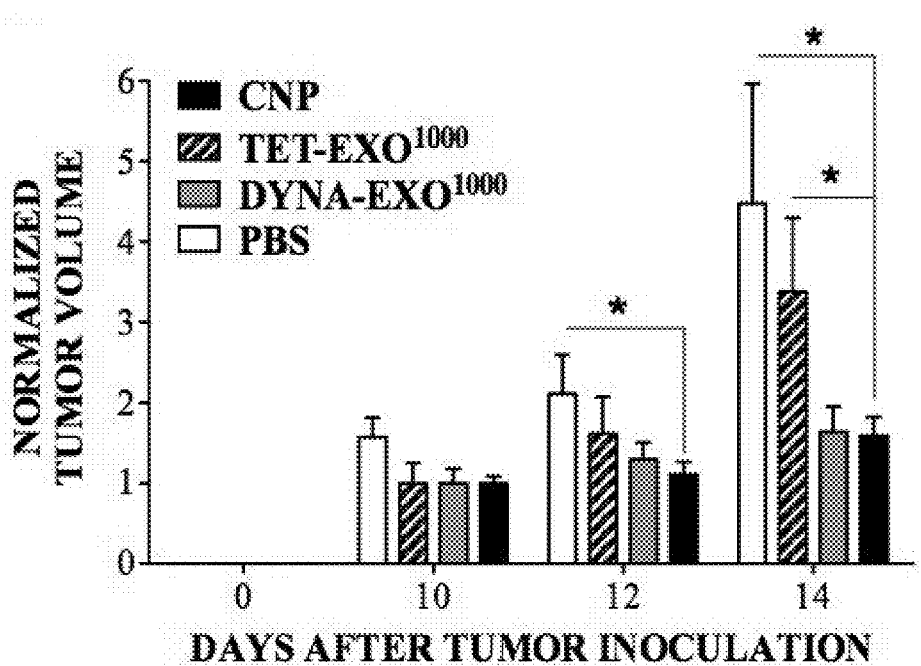
FIG. 27 is a bar graph showing the normalized tumor volume in C57BL/6 mice previously inoculated with B16F10-OVA for ten days, and injected peritumorally with 1.106 OT-1 CD8+ T cells. T cells were previously activated by CNPs or established controls containing a thousand fold higher exogenous IL-2 concentrations. Tumor volumes were normalized to volumes measured at day 10 for each group. The results are mean values from 6 mice per group, with error bars representing ±SEM. (*) represents p-value<0.05.
Figure 28:
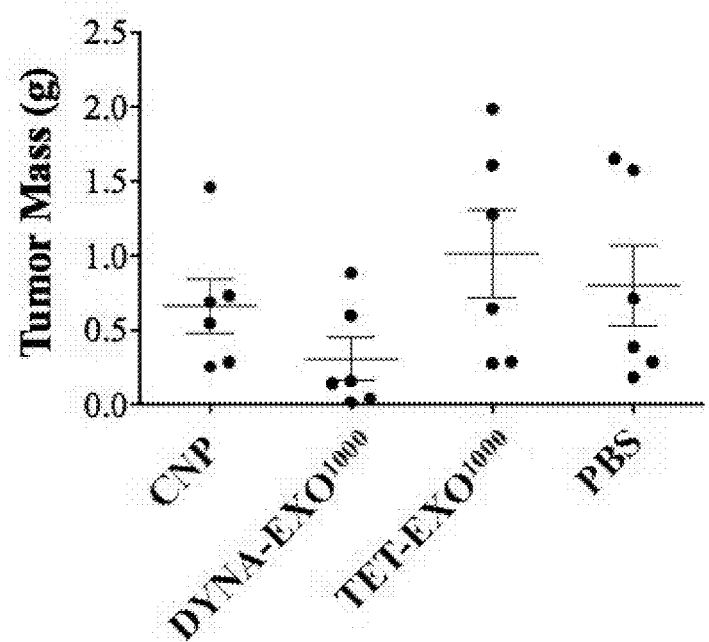
FIG. 28 is a graph showing measured tumor mass in C57BL/6 mice previously inoculated with B16F10-OVA for ten days, and injected peritumorally with 1.106 OT-1 CD8+ T cells. T cells were previously activated by CNPs or established controls containing a thousand fold higher exogenous IL-2 concentrations. Measurement of tumor mass for each group. Mice were euthanized directly before tumor mass determination; error bars represent ±SEM.
Figure 29:
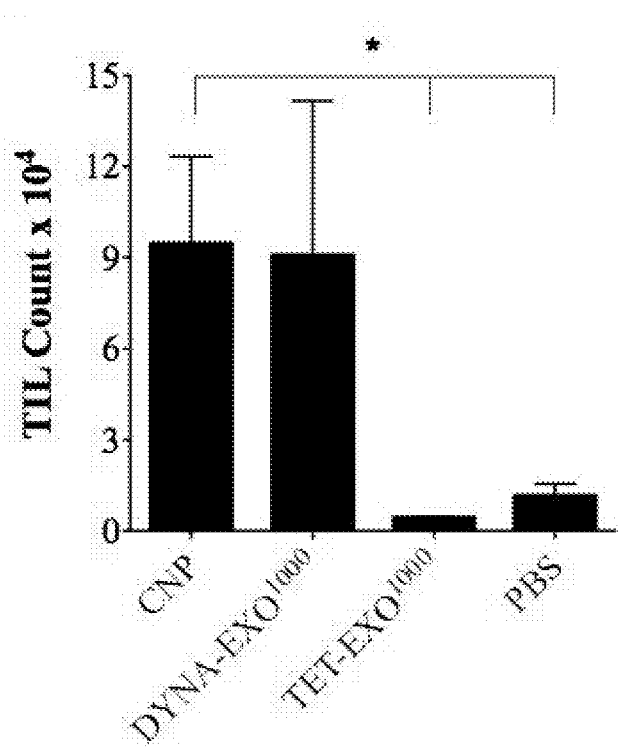
FIG. 29 is a bar graph showing the absolute number of activated T cells present in the tumor from C57BL/6 mice previously inoculated with B16F10-OVA for ten days, and injected peritumorally with $1\times10^6$ OT-1 CD8+ T cells per mouse; the T cells were previously activated by CNPs or established controls containing a thousand fold higher exogenous IL-2 concentrations. The results are mean values from 3 tumors per group; error bars represent ±SEM. (*) represents p-value<0.05.
Figure 30:
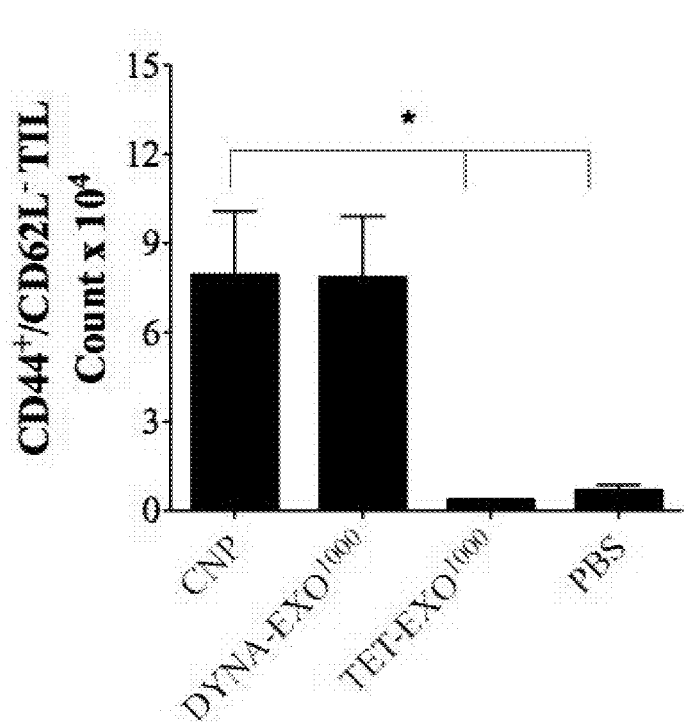
FIG. 30 is a bar graph showing the absolute number of CD44+/CD62L- effector T cells present in the tumor from C57BL/6 mice previously inoculated with B16F10-OVA for ten days, and injected peritumorally with $1\times10^6$ OT-1 CD8+ T cells per mouse; the T cells were previously activated by CNPs or established controls containing a thousand fold higher exogenous IL-2 concentrations. The results are mean values from 3 tumors per group; error bars represent ±SEM. (*) represents p-value<0.05.

We evaluated the effects of CNPs from Example 6 for adoptive therapy against an aggressive tumor model, the B16 mouse melanoma model, by transferring CD8+ T cells via a single peritumoral injection. Mice were inoculated with the B16 tumor for ten days before T cell injection. A significant delay in tumor growth at day 14 can be observed with animals adoptively transferred with CNP-cultured T cells compared to those without any treatment. Similar therapeutic effects with other platforms such as Dynabeads®, can be achieved but only with a thousand-fold more IL-2 (FIGS. 27 and 28). To elucidate the immunologic mechanisms behind the delayed tumor growth with CNP-cultured T cells, tumor-infiltrating lymphocytes (TILs) were harvested from the tumors of animals euthanized at day 14. Both the quantity and quality of TILs in animals adoptively transferred with CNP-cultured T cells were significantly different. A higher count of CD8+ T cells was detected in the tumor microenvironment, as indicated by the absolute number of isolated TILs per tumor in mice treated with CNP-stimulated T cells versus control platforms (FIG. 29). The high count of tumor-infiltrating CD8+ T cells in CNP-T cell cultured mice was measured to be similar to mice treated with T cells previously expanded using DYNA-EXO$^{1000}$, but at least an order of magnitude higher than other control groups. TILs isolated from tumors treated with CNP or DYNA-EXO$^{1000}$ were terminally differentiated into effectors as indicated by the high proportion of cells expressing a CD44+/CD62L− phenotype (FIG. 30). Histological evaluation of tumor tissue in the CNP group confirms evidence of lymphocyte infiltration, and apoptosis in the tumor cells. This was also observed in tumor tissues isolated from DYNA-EXO$^{1000}$ mice, but to a lesser extent in the tissues isolated from TET-EXO$^{1000}$ mice. As expected, tissue samples from tumors in mice receiving no treatment showed the highest extent of cytologic polymorphism. One notable difference was also the decrease in microvessel density observed in samples isolated from the CNPs and DYNA-EXO$^{1000}$; this was in addition to a decrease in tumor cell density as observed in the hematoxylin and eosin stain of tumor samples from mice euthanized at the end of the study. This decrease in tumor cell proliferation is consistent with the lack of new vasculature needed to supply the growing tumor mass.

We claim:

1. A carbon nanotube bundle comprising
   acid washed carbon nanotubes, the nanotubes having bound to or present on the surface
   one or more T cell receptor activators selected from the group consisting of antigens bound to WIC molecules and antibodies or fragments thereof that crosslink the T cell receptor/CD3 complex,
   one or more T cell costimulatory or T cell adhesion molecules, and
   polymeric nanoparticles comprising a cytokine encapsulated therein.

2. The carbon nanotube bundle of claim 1, wherein the carbon nanotubes are single-walled carbon nanotubes.

3. The carbon nanotube bundle of claim 1, wherein the one or more T cell receptor activators are non-covalently bound to the carbon nanotubes by adsorption.

4. The carbon nanotube bundle of claim 1, wherein the carbon nanotubes are treated with acid prior to adsorption of the one or more T cell receptor activators, and further treated with lithium borohydride.

5. The carbon nanotube bundle of claim 1, wherein the T cell receptor activator is a polyclonal T cell activator.

6. The carbon nanotube bundle of claim 1, wherein the T cell receptor activator comprises WIC molecules bound to peptide antigens.

7. The carbon nanotube bundle of claim 1, wherein the cytokine is IL-2.

8. The carbon nanotube bundle of claim 7, wherein the nanoparticle further comprises ferromagnetic and superparamagnetic materials.

9. The carbon nanotube bundle of claim 7, wherein the polymer is polylactic acid, polyglycolic acid, or polylactide-co-glycolide.

10. The carbon nanotube bundle of claim 1, further comprising a magnetic particle.

11. The carbon nanotube bundle of claim 10, wherein the magnetic particle is bound to or present on the nanotube.

12. The carbon nanotube bundle of claim 11, wherein the magnetic particle is magnetite.

13. The carbon nanotube bundle of claim 10, wherein the magnetic particle is selected from the group consisting of ferromagnetic and superparamagnetic materials.

14. The carbon nanotube bundle of claim 1, wherein the polymer of the nanoparticles is biodegradable.

\* \* \* \* \*

UNITED STATES PATENT AND TRADEMARK OFFICE
CERTIFICATE OF CORRECTION

PATENT NO. : 9,737,593 B2
APPLICATION NO. : 13/842782
DATED : August 22, 2017
INVENTOR(S) : Fahmy et al.

Page 1 of 1

It is certified that error appears in the above-identified patent and that said Letters Patent is hereby corrected as shown below:

On the Title Page

Item (72) Inventors, should read:
--Tarek M. Fahmy, New Haven, CT (US);
Lisa D. Pfefferle, Branford, CT (US);
Gary L. Haller, Hamden, CT (US); and
Tarek R. Fadel, Brookline, MA (US)--.

In the Specification

Column 1, Lines 18-21, replace "This invention was made with government support awarded by the National Science Foundation under Career Award Number 0747577 to Tarek M. Fahmy. The United States government has certain rights in this invention." with --This invention was made with government support under 0747577 awarded by National Science Foundation. The government has certain rights in the invention.--.

In the Claims

Claim 1, Column 52, Line 9, replace "WIC" with --MHC--.
Claim 6, Column 52, Line 28, replace "WIC" with --MHC--.
Claim 8, Column 52, Line 33, replace "nanoparticle further comprises" with --nanoparticles further comprise--.

Signed and Sealed this
Twelfth Day of May, 2020

Andrei Iancu
*Director of the United States Patent and Trademark Office*